United States Patent
Hosaka et al.

(10) Patent No.: US 12,376,781 B2
(45) Date of Patent: Aug. 5, 2025

(54) BRAIN WAVE ANALYSIS DEVICE, BRAIN WAVE ANALYSIS SYSTEM, AND BRAIN WAVE ANALYSIS PROGRAM

(71) Applicant: Mitsubishi Tanabe Pharma Corporation, Osaka (JP)

(72) Inventors: Toshihiro Hosaka, Osaka (JP); Hiroshi Sato, Osaka (JP); Makoto Tamura, Osaka (JP); Ryuta Saito, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 975 days.

(21) Appl. No.: 17/285,160

(22) PCT Filed: Oct. 15, 2019

(86) PCT No.: PCT/JP2019/040463
§ 371 (c)(1),
(2) Date: Apr. 14, 2021

(87) PCT Pub. No.: WO2020/080354
PCT Pub. Date: Apr. 23, 2020

(65) Prior Publication Data
US 2021/0321929 A1    Oct. 21, 2021

(30) Foreign Application Priority Data

Oct. 15, 2018 (JP) .................. 2018-194497

(51) Int. Cl.
| | | |
|---|---|---|
| A61B 5/383 | (2021.01) | |
| A61B 5/00 | (2006.01) | |
| A61B 5/374 | (2021.01) | |

(52) U.S. Cl.
CPC .............. *A61B 5/383* (2021.01); *A61B 5/374* (2021.01); *A61B 5/4809* (2013.01);
(Continued)

(58) Field of Classification Search
None
See application file for complete search history.

(56) References Cited

U.S. PATENT DOCUMENTS

| | | | |
|---|---|---|---|
| 2014/0242559 A1* | 8/2014 | Patel ................... | G09B 5/00 434/236 |
| 2014/0316230 A1* | 10/2014 | Denison ............... | A61B 5/168 600/545 |

(Continued)

FOREIGN PATENT DOCUMENTS

| | | |
|---|---|---|
| CN | 103919565 A | 7/2014 |
| JP | 2017-192425 A | 10/2017 |
| KR | 10-2016-0034227 A | 3/2016 |

OTHER PUBLICATIONS

Extended European Search Report issued in corresponding European Patent Application No. 19874500.2 dated May 25, 2022.
(Continued)

*Primary Examiner* — Jason M Sims
*Assistant Examiner* — Matthew Eric Ogles
(74) *Attorney, Agent, or Firm* — Morgan, Lewis & Bockius LLP

(57) ABSTRACT

The present disclosure provides a brain wave analysis device with a computation section configured to compute a first ratio and a second ratio from a spectrum obtained by performing frequency analysis on time-series data of brain waves measured at a predetermined location of a head of a subject.

14 Claims, 33 Drawing Sheets

(52) U.S. Cl.
CPC .......... *A61B 5/4824* (2013.01); *A61B 5/7203* (2013.01); *A61B 2560/02* (2013.01)

(56) References Cited

U.S. PATENT DOCUMENTS

| | | | |
|---|---|---|---|
| 2016/0022168 A1 | 1/2016 | Luczak et al. | |
| 2016/0296164 A1* | 10/2016 | Garcia Molina | ...... A61B 5/372 |
| 2018/0140249 A1* | 5/2018 | Frohlich | .............. A61B 5/4812 |
| 2020/0105398 A1* | 4/2020 | Chen | ....................... G06F 3/015 |

OTHER PUBLICATIONS

International Search Report issued in corresponding International Patent Application No. PCT/JP2019/040463 dated Dec. 10, 2019.
Office Action dated Feb. 29, 2024, issued in corresponding Chinese Patent Application No. 201980067324.8.

* cited by examiner

FIG.2

MICE

| WAVE TYPE | FREQUENCY BAND | STATE OF CONSCIOUSNESS | | DESCRIPTOR |
|---|---|---|---|---|
| γ4 (GAMMA) | 120 Hz - 150 Hz | GENERATED IN STRESS-INDUCED STATE(NERVOUS, ANXIOUS, IRRITATED, EXCITED) | STRESSED | FIRST FREQUENCY BAND |
| γ3 (GAMMA) | 90 Hz – 120 Hz | | | |
| γ2 (GAMMA) | 60 Hz – 90 Hz | | | |
| γ1 (GAMMA) | 30 Hz – 60 Hz | | | |
| β (BETA) | 12 Hz – 30 Hz | GENERATED IN NORMAL AWAKE STATE/ACTIVE STATE | AWAKE | SECOND FREQUENCY BAND |
| θ (THETA) | 4 Hz – 12 Hz | GENERATED DURING LIGHT SLEEP (MEDITATION, DOZING) | SLEEPING | THIRD FREQUENCY BAND |
| δ (DELTA) | 1 Hz – 4 Hz | GENERATED DURING DEEP SLEEP | | |

HUMANS

| WAVE TYPE | FREQUENCY BAND | STATE OF CONSCIOUSNESS | | DESCRIPTOR |
|---|---|---|---|---|
| HIGH γ (GAMMA) | 52 Hz – 82.25 Hz | GENERATED IN STRESS-INDUCED STATE (NERVOUS,ANXIOUS, IRRITATED,EXCITED) | STRESSED | FIRST FREQUENCY BAND |
| MID-RANGE γ (GAMMA) | 41 Hz – 48 Hz | | | |
| LOW γ (GAMMA) | 31 Hz – 40 Hz | | | |
| HIGH β (BETA) | 18 Hz – 29.75 Hz | GENERATED IN NORMAL AWAKE STATE/ACTIVE STATE | AWAKE | SECOND FREQUENCY BAND |
| LOW β (BETA) | 13 Hz – 16.75 Hz | | | |
| HIGH α (ALPHA) | 10 Hz – 11.75 Hz | GENERATED IN RESTING STATE /RELAXED STATE | RELAXED | FOURTH FREQUENCY BAND |
| LOW α (ALPHA) | 7.5 Hz – 9.25 Hz | | | |
| θ (THETA) | 3.5 Hz – 6.75 Hz | GENERATED DURING LIGHT SLEEP (MEDITATION, DOZING) | ASLEEP | THIRD FREQUENCY BAND |
| δ (DELTA) | 0.5 Hz – 2.75 Hz | GENERATED DURING DEEP SLEEP | | |

1/4 Hz (FREQUENCY)

BRAIN WAVE ANALYSIS DEVICE, BRAIN WAVE ANALYSIS SYSTEM, AND BRAIN WAVE ANALYSIS PROGRAM

TECHNICAL FIELD

Technology of the present invention relates to a brain wave analysis device, a brain wave analysis system, and a brain wave analysis program.

BACKGROUND ART

Devices are known in which multiple electrodes are employed to measure brain waves, and a subject state is inferred based on the measured brain waves (see, for example, Patent Document 1).

PATENT DOCUMENTS

Patent Document 1: Japanese Patent Application Laid-Open (JP-A) No. 2017-192425

SUMMARY OF INVENTION

Technical Problem

However, in the device disclosed in Patent Document 1, although brain waves are detected with high precision, it is necessary to attach a large number of electrodes to the subject. Since the requirement for a large number of electrodes limits the actions of the subject, it is not feasible to measure brain waves and infer a subject state when the subject is in an everyday environment.

An object of the present invention is to provide a brain wave analysis device, a brain wave analysis system, and a brain wave analysis program that enable evaluation of sensations and functional changes such as focus or pain stimulated by environmental stimulation or physical sensations by simpler measurement than in cases in which plural electrodes are attached.

Solution to Problem

An aspect of the present disclosure is a brain wave analysis device including a computation section configured to compute a first ratio and a second ratio from a spectrum obtained by performing frequency analysis on time-series data of brain waves measured at a predetermined location of a head of a subject. The first ratio is either a ratio, with respect to a feature value that is a strength of one wave in a first frequency band generated in a stress-induced state, of a feature value that is a strength of another wave in the first frequency band present in a frequency band higher than the one wave, or a ratio of a feature value that is a strength of a wave in the first frequency band with respect to a feature value that is a strength of a wave in a second frequency band generated in an awake state. The second ratio is a ratio of a feature value that is a strength of a wave in a third frequency band generated in a sleeping state with respect to a feature value that is a strength of a wave in the second frequency band generated in an awake state. The brain wave analysis device also includes an inference section configured to infer a subject based on the first ratio, a first reference value set using the first ratio, the second ratio, and a second reference value set using the second ratio.

In the first aspect, the first reference value is either an average of the first ratio for all measurement timings, an average of the first ratio for a period prior to stimulation, an average of the first ratio for a period of stimulation, an average of the first ratio for a period after the period of stimulation has ended, or an average of the first ratio for a period of non-stimulation. The second reference value is either an average of the second ratio for all measurement timings, an average of the second ratio for a period prior to stimulation, an average of the second ratio for a period of stimulation, an average of the second ratio for a period after the period of stimulation has ended, or an average of the second ratio for a period of non-stimulation. Note that the first reference value is an average such as an arithmetic mean, weighted average, or a root-mean-square of the first ratio or of a natural logarithm value converted from the first ratio, or is a median value of the first ratio or of a natural logarithm value converted from the first ratio. The second reference value is an average such an arithmetic mean, a weighted average, or a root-mean-square of the second ratio or of a natural logarithm value converted from the second ratio, or is a median value of the second ratio or of a natural logarithm value converted from the second ratio. In cases in which the average or median value is a value converted into a natural logarithm, an antilogarithm of this value may be employed as the reference value.

In the first aspect, the inference section is configured to infer the state of the subject by determining into which quadrant a point corresponding to the first ratio and the second ratio computed by the computation section falls in a two-dimensional coordinate system having the first reference value and the second reference value at the origin and the first ratio on one axis and the second ratio on another axis.

In the first aspect, the inference section is configured to infer a level of the state of the subject by further employing at least one of a distance of the point from the origin, a distance of the point from the origin in a direction of the one axis, a distance of the point from the origin in a direction of the other axis, or an appearance frequency with which points appear in the same quadrant within a predetermined period.

In the first aspect, the inference section is configured to infer the state of the subject based on a difference between the first ratio computed by the computation section and the first reference value and based on a difference between the second ratio computed by the computation section and the second reference value, and by determining for the first ratio and the second ratio computed by the computation section whether, the first ratio is equal to or greater than the first reference value and the second ratio is equal to or greater than the second reference value, the first ratio is equal to or greater than the first reference value and the second ratio is lower than the second reference value, the first ratio is lower than the first reference value and the second ratio is equal to or greater than the second reference value, or the first ratio is lower than the first reference value and the second ratio is lower than the second reference value.

In the first aspect, waves in the first frequency band are gamma waves, waves in the second frequency band are beta waves, and waves in the third frequency band are either theta waves or delta waves.

In the first aspect, the spectrum is a spectrum from which a noise component having a third ratio exceeding a third reference value has been removed, the third ratio being a ratio of a feature value that is a strength of a wave in the first frequency band or a wave in the second frequency band with respect to a feature value that is a strength of a wave in a fourth frequency band that is lower than the second frequency band and higher than the third frequency band.

In the first aspect, the noise component is a component in which the third ratio exceeds the third reference value, the third ratio being a ratio of a feature value that is a strength of a low gamma wave in the first frequency band or a strength of a high beta wave in the second frequency band with respect to a feature value that is a strength of a low alpha wave in the fourth frequency band.

In the first aspect, the feature value wave strength is an average such as an arithmetic mean, a weighted average, or a root-mean-square of the strength of waves belonging to the same frequency band or the strength of these waves converted into a natural logarithm value, is a maximum strength of these waves, is an integrated value of strengths of these waves, or is a median value of strengths of these waves. Alternatively, in cases in which the feature value wave strength is a value converted from the wave strength into a natural logarithm, an antilogarithm value of this value may be employed.

In the first aspect, the state of the subject is either an attentive state, a focused state, or a distracted state.

In the first aspect, the state of the subject is a state in which pain is felt.

A second aspect of the present disclosure is a brain wave analysis device including a computation section and an inference section. The computation section is configured to compute a first ratio and a difference amount or a fourth ratio from a spectrum obtained by performing frequency analysis on time-series data of brain waves measured at a predetermined location of a head of a subject. The first ratio is either a ratio, with respect to a feature value that is a strength of one wave in a first frequency band generated in a stress-induced state, of a feature value that is a strength of another wave in the first frequency band present in a frequency band higher than the one wave, or a ratio of a feature value that is a strength of a wave in the first frequency band with respect to a feature value that is a strength of a wave in a second frequency band generated in an awake state. The difference amount is an amount obtained from feature values of the strengths of waves in bands resulting from splitting in two a band of frequency equal to or greater than a third frequency band generated in a sleeping state and lower than the second frequency band, and the fourth ratio is a ratio of the feature values of the strengths of waves in the resulting split bands. The inference section is configured to infer a state of the subject based on the first ratio, a first reference value set using the first ratio, the difference amount or the fourth ratio, and a second reference value set using the difference amount or the fourth ratio.

In the second aspect, the difference amount is a difference between a strength or power value integral of a region on a low frequency side and a strength or power value integral of a region on a high frequency side. For example, the difference amount is a value of the strength or power value integral of the high frequency side region subtracted from the strength or power value integral of the low frequency side region.

In the second aspect, the fourth ratio is a ratio between the strength or power value integral of the high frequency side region and the strength or power value integral of the low frequency side region. For example, the fourth ratio is a ratio of the strength or power value integral of the low frequency side region with respect to the strength or power value integral of the high frequency side region.

In the second aspect, the difference amount is a difference between a maximum power value of a region on a low frequency side and a minimum power value of a region on a high frequency side.

A third aspect of the present disclosure is a brain wave analysis system including a data acquisition section configured to acquire time-series data of brain waves measured at a predetermined location of a head of a subject, and the brain wave analysis device described above.

A fourth aspect of the present disclosure is a brain wave analysis program executable by a computer to perform processing, the processing including computing a first ratio and a second ratio from a spectrum obtained by performing frequency analysis on time-series data of brain waves measured at a predetermined location of a head of a subject. The first ratio is either a ratio, with respect to a feature value that is a strength of one wave in a first frequency band generated in a stress-induced state, of a feature value that is a strength of another wave in a first frequency band present in a frequency band higher than the one wave, or a ratio of a feature value that is a strength of a wave in a second frequency band generated in an awake state with respect to a feature value that is a strength of a wave in the first frequency band. The second ratio is a ratio of a feature value that is a strength of a wave in a third frequency band generated in a sleeping state with respect to a feature value that is a strength of a wave in the second frequency band generated in an awake state. The processing also includes inferring a state of the subject based on the first ratio, a first reference value set using the first ratio, the second ratio, and a second reference value set using the second ratio.

A fifth aspect of the present disclosure executable by a computer to perform processing including a computation step and an inference step. The computation step includes computing a first ratio and a difference amount from a spectrum obtained by performing frequency analysis on time-series data of brain waves measured at a predetermined location of a head of a subject. The first ratio is either a ratio, with respect to a feature value that is a strength of one wave in a first frequency band generated in a stress-induced state, of a feature value that is a strength of another wave in a first frequency band present in a frequency band higher than the one wave, or a ratio of a feature value that is a strength of a wave in the first frequency band with respect to a feature value that is a strength of a wave in a second frequency band generated in an awake state. The difference amount is an amount obtained from feature values of the strengths of waves in bands resulting from splitting in two a band of frequency equal to or greater than a third frequency band generated in a sleeping state and lower than the second frequency band. The inference step includes inferring a state of the subject based on the first ratio, a first reference value set using the first ratio, the difference amount, and a second reference value set using the difference amount.

Advantageous Effects of Invention

The first aspect to the fifth aspect of the present disclosure enable an everyday state of the subject to be inferred by simple measurement.

BRIEF DESCRIPTION OF DRAWINGS

FIG. 2 is a diagram illustrating brain wave categories for mice and for humans.

DESCRIPTION OF EMBODIMENTS

Figure 1:
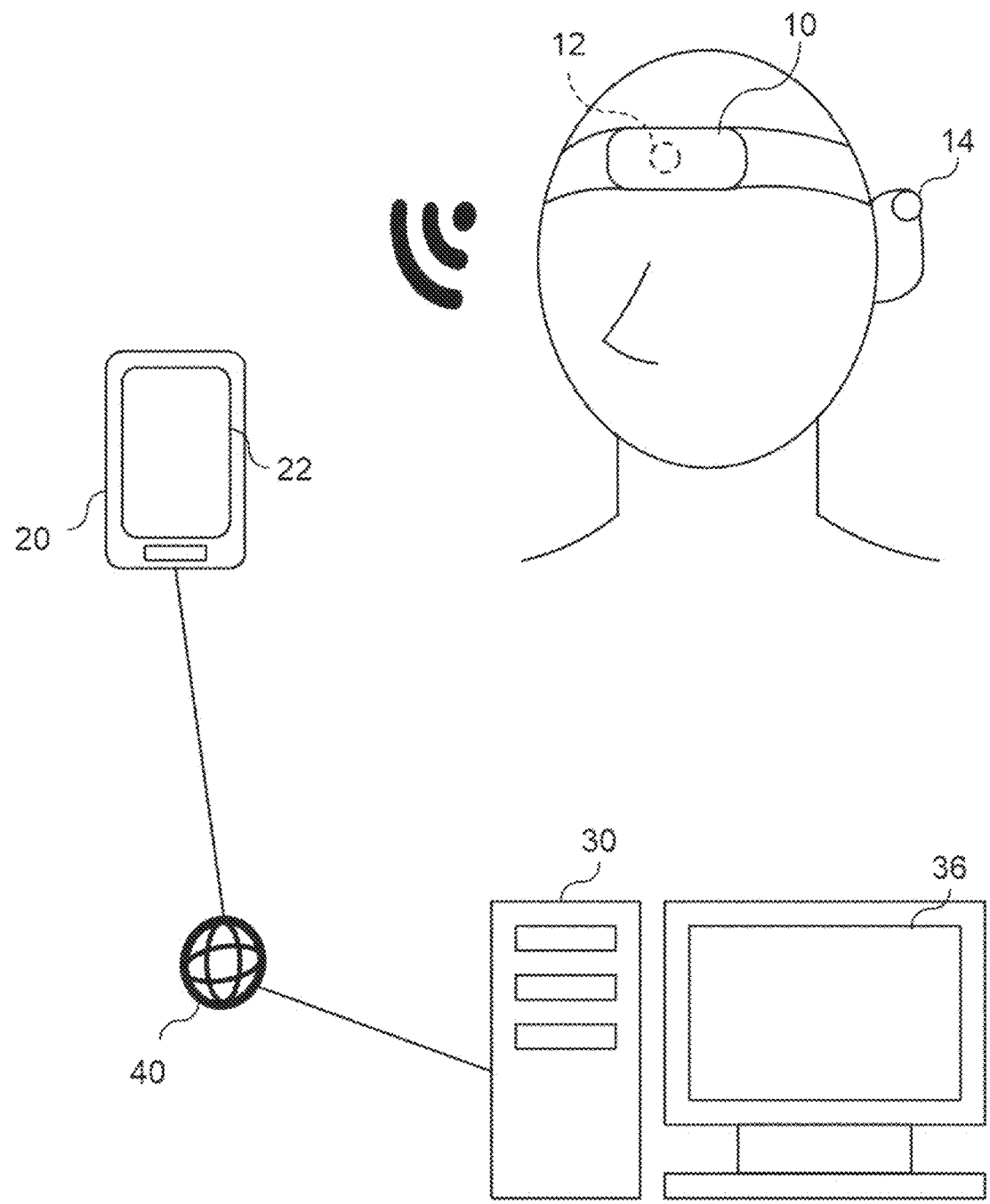
FIG. 1 is a diagram illustrating an example of a brain wave analysis system according to an exemplary embodiment.

Explanation follows regarding an example of an exemplary embodiment of technology of the present invention, with reference to the drawings. Note that in each of the drawings, the same or equivalent configuration elements and sections will be allocated the same reference numerals. Scale and proportions in the drawings may be exaggerated to aid explanation, and may not conform to the actual proportions.

FIG. 1 illustrates an example of a brain wave analysis system according to a present exemplary embodiment.

As illustrated in FIG. 1, the brain wave system includes a data acquisition section 10, a mobile terminal 20, and a brain wave analysis device 30.

The data acquisition section 10 is, for example, attached to the forehead or a side or the back of the head of a subject in order to detect brain waves of the subject and acquire brain wave data. The data acquisition section 10 includes at least one electrode 12 that is placed in contact with the subject. The electrode 12 detects changes in potential occurring in the cerebral cortex as brain waves. The data acquisition section 10 includes a non-illustrated transmission section. The data acquisition section 10 transmits the acquired brain wave data to the mobile terminal 20 through the transmission section. The data acquisition section 10 further includes a reference electrode 14. The reference electrode 14 is, for example, attached to an ear of the subject. The data acquisition section 10 transmits data expressing changes in potential between the electrode 12 and the reference electrode 14 to the mobile terminal 20 through the transmission section. Note that the term "subject" employed in the present specification is not limited to human subjects. Such subjects may include any animal for which brain wave detection is possible. In cases in which the subject is non-human, the electrode 12 and the reference electrode 14 are attached at positions deemed appropriate by a practitioner skilled in the art.

The mobile terminal 20 is carried by the subject, and collects brain wave data acquired by the data acquisition section 10. The collected brain wave data is transmitted to the brain wave analysis device 30 through a communication network 40 such as the internet at predetermined timings. The brain wave analysis device 30 analyzes the brain waves. This brain wave analysis will be described in detail later.

In the example illustrated in FIG. 1, the brain wave data is initially collected in the mobile terminal 20 before being transmitted to the brain wave analysis device 30. However, the brain wave data acquired by the data acquisition section 10 may be transmitted directly to the brain wave analysis device 30. In such cases, the brain wave data may be transmitted from the data acquisition section 10 to the brain wave analysis device 30 either wirelessly or through a wired connection.

Analysis results of the analysis by the brain wave analysis device 30 are displayed on at least one out of a display section 22 provided to the mobile terminal 20 or a display section 36 of the brain wave analysis device 30. The analysis results can thus be confirmed by at least one out of the subject or an analyst.

FIG. 2 is a diagram illustrating brain wave classifications for mice and for humans. The upper table in FIG. 2 illustrates mouse brain wave classifications, and the lower table in FIG. 2 illustrates human brain wave classifications.

The brain waves acquired by the data acquisition section 10 in FIG. 1 includes waves in plural frequency bands. Each frequency bands has its own name. FIG. 2 illustrates mouse brain waves in addition to human brain waves. Since explanation is also given regarding mouse testing in the forthcoming Examples, explanation now follows regarding brain waves that are similar in both mice and humans.

Brain wave frequency bands may be classified in various ways, and the illustrated classifications are merely one example thereof. The brain wave analysis system of the present exemplary embodiment may be applied even if the frequency band classifications are shifted somewhat from those illustrated in FIG. 2.

First, explanation follows regarding mouse brain waves.

Mouse brain waves are broadly classified into first frequency band waves, second frequency band waves, and third frequency band waves. The first frequency band waves often appear in a state in which stress is induced. The second frequency band waves often appear in a normal awake state. The third frequency band waves often appear in a sleeping state.

Considered in sequence from the highest frequency band, the first frequency band includes gamma 4 waves to gamma 1 waves, the second frequency band includes beta waves, and the third frequency band includes theta waves and delta waves.

Human brain waves are classified into the first to the third frequency bands, and additionally into a fourth frequency band. The first frequency band waves often appear in a stress-induced state. The second frequency band waves often appear in a normal awake state. The third frequency band waves often appear in a sleeping state. The fourth frequency band often appears in a relaxed state.

Considered in sequence from the highest frequency band, the first frequency band includes high gamma waves, mid-range gamma waves, and low gamma waves, the second frequency band includes high beta waves and low beta waves, the fourth frequency band includes high alpha waves and low alpha waves, and the third frequency band includes theta waves and delta waves. The respective wave frequency bands are named differently depending on whether referring to mice or humans. However, it is known that waves expressed using the same Greek letters share similar characteristics in both humans and mice.

Next, explanation follows regarding a hardware configuration of the brain wave analysis device 30.

Figure 3:
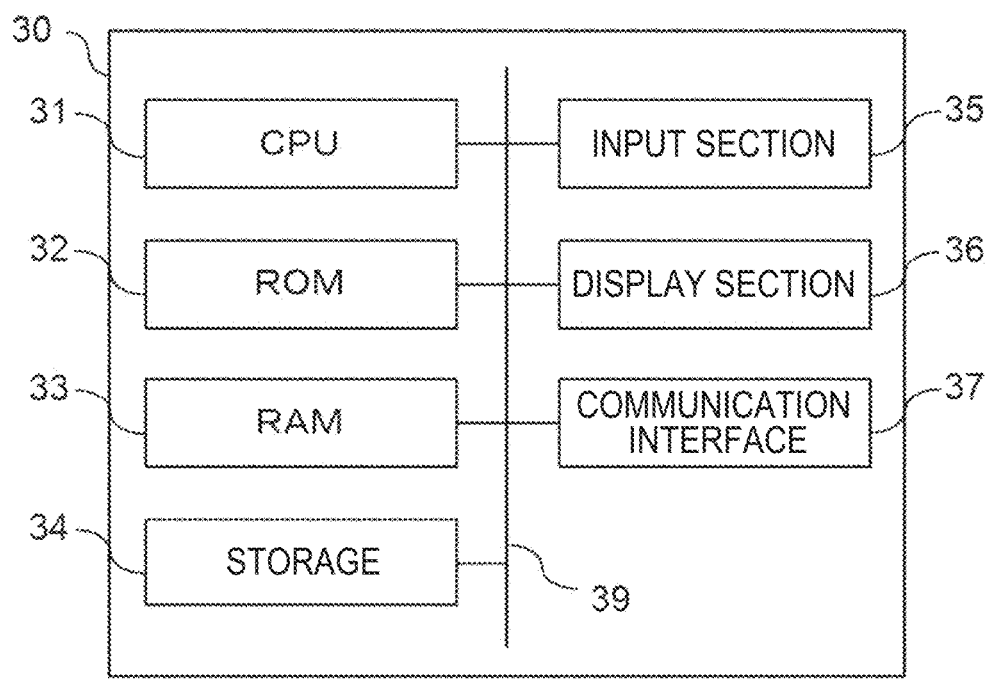
FIG. 3 is a block diagram illustrating a hardware configuration of a brain wave analysis device.

FIG. 3 is a block diagram illustrating a hardware configuration of the brain wave analysis device.

As illustrated in FIG. 3, the brain wave analysis device 30 includes a central processing unit (CPU) 31, read only memory (ROM) 32, random access memory (RAM) 33, storage 34, an input section 35, the display section 36, and a communication interface (I/F) 37. Each of these configurations are connected together through a bus 39 so as to be capable of communicating with each other.

The CPU 31 is a central processing unit that executes various programs and controls various sections. Namely, the CPU 31 reads a program from the ROM 32 or the storage 34, and executes the program using the RAM 33 as a workspace. The CPU 31 controls the various configurations described above and performs various computation processing according to the program recorded in the ROM 32 or the storage 34. In the present exemplary embodiment, a brain wave analysis program for analyzing brain waves is held in either the ROM 32 or the storage 34.

The ROM 32 holds various programs and various data. The RAM 33 serves as a workspace that temporarily stores programs and data. The storage 34 is configured by a hard disk drive (HDD) or a solid state drive (SSD), and holds various programs including an operating system, and various data.

The input section 35 includes a pointing device such as a mouse, and a keyboard, and is used to perform various input. The display section 36 is a liquid crystal display configured to display various information. The display section 36 may employ a touch panel format and also function as the input section 35.

The communication interface 37 is an interface used to communicate with other devices, such as the data acquisition section 10 and the mobile terminal 20, and employs a protocol such as Ethernet (registered trademark), FDDI, Wi-Fi (registered trademark), Bluetooth (registered trademark), or the like.

Next, explanation follows regarding functional configuration of the brain wave analysis device 30.

Figure 4:
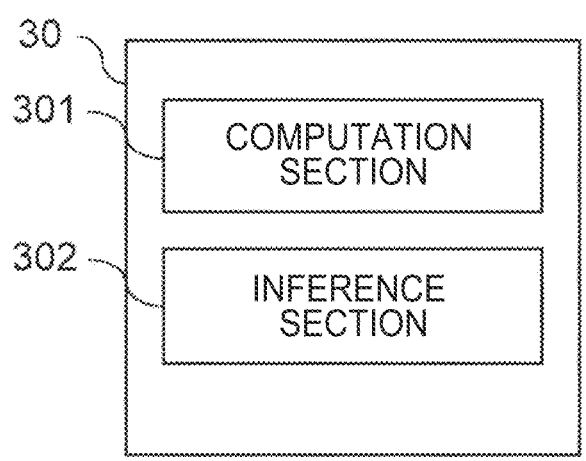
FIG. 4 is a block diagram illustrating an example of functional configuration of a brain wave analysis device.

FIG. 4 is a block diagram illustrating an example of functional configuration of the brain wave analysis device.

As illustrated in FIG. 4, the functional configuration of the brain wave analysis device 30 includes a computation section 301 and an inference section 302. Each of the functional configurations is implemented by the CPU 31 reading the brain wave analysis program stored in the ROM 32 or the storage 34, expanding the program in the RAM 33, and executing the program.

The computation section 301 computes a first ratio and a second ratio from a spectrum obtained by performing frequency analysis on time-series data of brain waves measured at a predetermined location of the head of the subject. In order to compute the first ratio and the second ratio, the computation section 301 extracts waves of two specific frequencies from the spectrum and computes a ratio of feature values that are strengths of the extracted waves. Note that the predetermined location may be the forehead, or the side or rear of the head of the subject, as described above. Spectra include amplitude spectra and power spectra. The following explanation describes a case in which an amplitude spectrum is obtained by frequency analysis.

The first ratio is a ratio, with respect to a feature value that is a strength of one wave in a first frequency band generated in a stress-induced state, of a feature value that is a strength of another wave in the first frequency band present in a frequency band higher than the one wave. In such cases, the first ratio is, for example, the ratio of a high gamma wave strength with respect to a low gamma wave strength in the first frequency band illustrated in FIG. 2. Alternatively, the first ratio may be a ratio of a feature value that is a strength of a wave in the first frequency band with respect to a feature value that is a strength of a wave in the second frequency band generated in an awake state. In such cases, the first ratio is, for example, the ratio of a wave strength feature value of a high gamma wave or a mid-range gamma wave in the first frequency band with respect to a wave strength feature value of a high beta wave in the second frequency band illustrated in FIG. 2. In the case of a mouse, the first ratio is, for example, a ratio of a gamma 3 or a gamma 4 wave with respect to a gamma 1 wave, or a wave strength feature value of a gamma 2 wave, a gamma 3 wave, or a gamma 4 wave with respect to a wave strength feature value of a beta wave.

The second ratio is a ratio of a feature value that is a strength of a wave in the third frequency band generated in a sleeping state with respect to a feature value that is a strength of a wave in the second frequency band generated in an awake state. For example, the second ratio is a ratio of the wave strength feature value of a theta wave or a delta wave in the third frequency band with respect to a wave strength feature value of either all beta waves, or a high beta wave or low beta wave, in the second frequency band illustrated in FIG. 2. In the case of a mouse, the second ratio is, for example, a ratio of a wave strength feature value of a theta wave with respect to all beta waves.

The wave strength feature value may be the average wave strength, maximum wave strength, integrated value of wave strengths, or median wave strength of waves belonging in the same frequency band. Here, the wave strength feature values of waves in the (first, second, or third) frequency bands may be derived or computed from part of the corresponding frequency band, or may be derived or computed from all of the corresponding frequency band. For example, the wave strength of a specific frequency in the corresponding frequency band may be taken as the wave strength feature value in the corresponding frequency band. Alternatively, the average wave strength, integrated value of wave strengths, median wave strength, or maximum wave strength of waves belonging a frequency band representing some or all of the corresponding frequency band may be taken as the wave strength feature value in the corresponding frequency band. Alternatively, plural frequency bands in the corresponding frequency band may be set, and the average wave strength, integrated value of wave strengths, median wave strength, or maximum wave strength of waves belonging to each of these set frequency bands may be computed, and an average or sum of the computed values may be taken as the wave strength feature value in the corresponding frequency band. Note that the average in the above description may be any value out of the arithmetic mean, a weighted average, a geometric average, or a root-mean-square. Note that wave strength corresponds to an amplitude value in cases in which the spectrum employed is an amplitude spectrum, and corresponds to a power value in cases in which the spectrum employed is a power spectrum. The following explanation describes an example in which amplitude is employed as the wave strength.

The inference section 302 infers a subject state based on the first ratio, a first reference value set using the first ratio, the second ratio, and a second reference value set using the second ratio. The first reference value, the second reference value, and inference of the subject state will be described later.

Next, explanation follows regarding operation of the brain wave analysis device 30.

Figure 5:
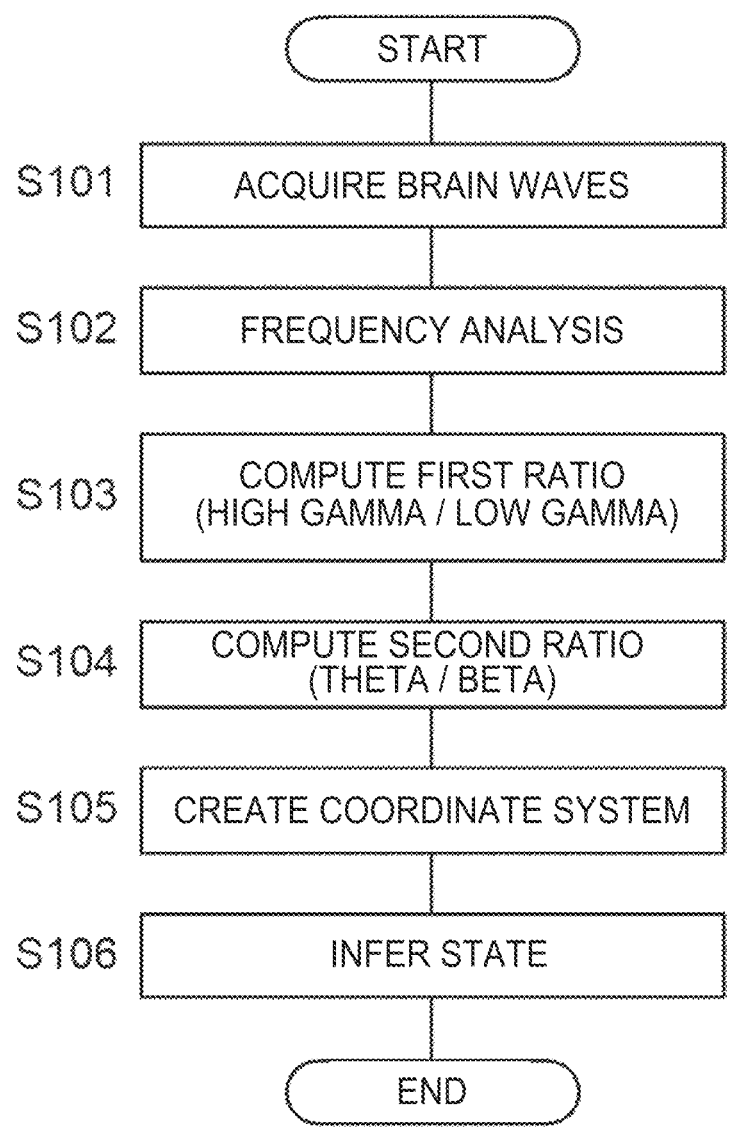
FIG. 5 is a flowchart illustrating a flow of brain wave analysis processing by an image forming device.
Figure 6:
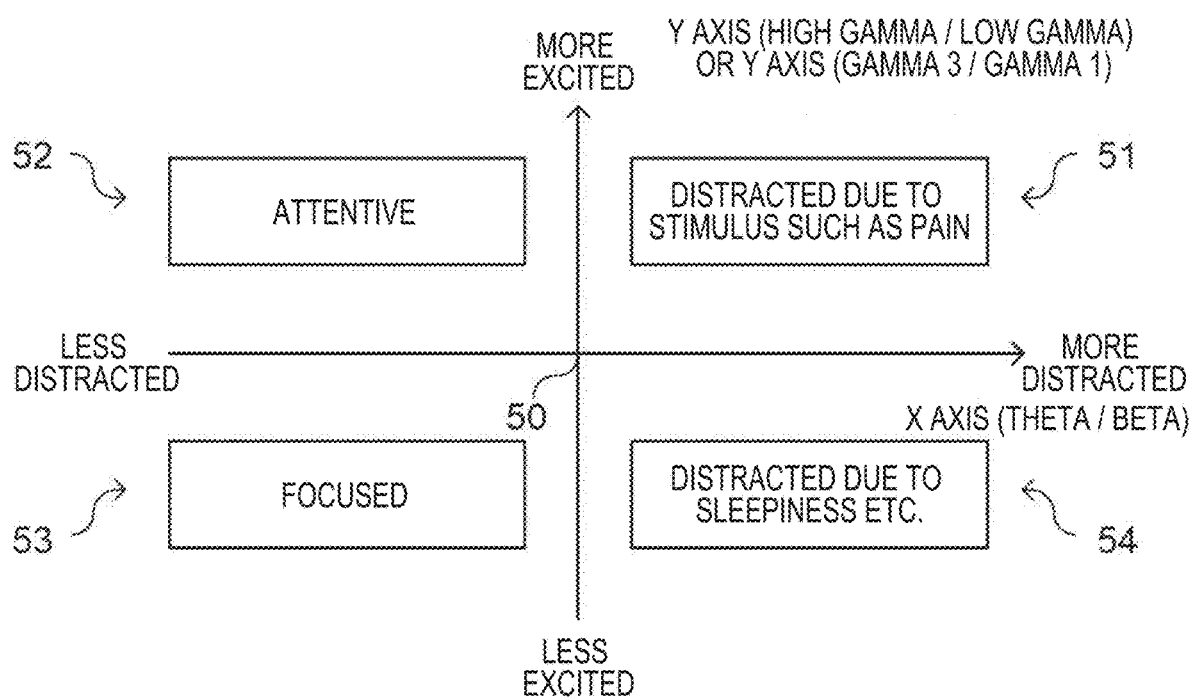
FIG. 6 is a diagram illustrating subject states expressed by a coordinate system.

FIG. 5 is a flowchart illustrating a flow of brain wave analysis processing by an image forming device. The CPU 31 reads the brain wave analysis program from the ROM 32 or the storage 34, expands the program in the RAM 33, and executes the program in order to perform the brain wave analysis processing. FIG. 6 is a diagram illustrating subject states on a coordinate system.

The CPU 31 acquires brain wave data obtained by measuring brain waves of the subject at predetermined timings (step S101). This brain wave data is received from either the data acquisition section 10 or the mobile terminal 20 as described above.

The CPU 31 then performs amplitude conversion for each frequency band of the brain waves using a Fourier transform method or the like to obtain an amplitude spectrum (step S102).

The CPU 31 then employs the amplitude spectrum obtained by the Fourier transform to compute the first ratio (step S103). Explanation follows regarding a case in which the CPU 31 computes a ratio of a high gamma wave amplitude with respect to a low gamma wave amplitude as an example of the first ratio. The CPU 31 thus extracts a low gamma wave component and a high gamma wave component from the amplitude spectrum to compute such an amplitude ratio at each timing.

The CPU 31 then employs the amplitude spectrum obtained by the Fourier transform to compute the second ratio (step S104). Explanation follows regarding a case in which the CPU 31 computes a ratio of a theta wave amplitude with respect to a beta wave amplitude as an example of the second ratio. The CPU 31 thus extracts a beta wave component and a theta wave component from the amplitude spectrum to compute such an amplitude ratio at each timing.

The CPU 31 then employs the first ratio and the second ratio to create a coordinate system (step S105). Specifically, as the first reference value, the CPU 31 takes, for all brain wave measurement timings, an average value found by an arithmetic mean, a weighted average, or using a root-mean-square method for the first ratio or a natural logarithm value converted from the first ratio, takes a median value of the first ratio or of a natural logarithm value converted from the first ratio, or takes an antilogarithm value of the aforementioned average or median value. As the second reference value, for all measurement timings, the CPU 31 takes an average value found by an arithmetic mean, a weighted average, or using a root-mean-square method for the second ratio or a natural logarithm value converted from the second ratio, takes a median value of the second ratio or of a natural logarithm value converted from the second ratio, or takes an antilogarithm value of the average or median value. Then, as illustrated in FIG. 6, the CPU 31 creates a coordinate system having the first reference value and the second reference value at the origin and the first ratio on the vertical axis (Y axis) and the second ratio on the horizontal axis (X axis). Note that as long as the first ratio is on the vertical axis (Y axis) and the second ratio is on the horizontal axis (X axis), the origin does not necessarily have to be the first reference value and the second reference value. Explanation follows regarding a coordinate system in which the first reference value and the second reference value are at the origin. Moreover, the first reference value and the second reference value do not have to be averages for all brain wave measurement timings. Averages for a period prior to stimulation, averages for a period of stimulation, or averages for a period after the period of stimulation may be employed therefor. Explanation follows regarding a case in which averages for all measurement timings are found as the first reference value and the second reference value.

The CPU 31 employs the created coordinate system to infer the subject state (step S106). In the created coordinate system, the larger the vertical axis value, the more excited the subject state. The larger the horizontal axis value, the more distracted the subject state. For each event (unit time), a combination of the first ratio and the second ratio is plotted as a point on the created coordinate system in order to observe the appearance frequency in the same quadrant and shifts in the plot positions. There is no limitation to plotting the points using combinations of the first ratio and the second ratio based on units of time. For example, the points may be plotted using combinations of average values of the first ratio and average values of the second ratio between plural consecutive units of time (for example between 1 second and 5 seconds).

The quadrants are split into a first quadrant 51 to a fourth quadrant 54. Points having both an X axis value and a Y axis value equal to or greater than the first reference value and the second reference value respectively fall into the first quadrant 51. Points having an X axis value lower than the first reference value and a Y axis value equal to or greater than the second reference value fall into the second quadrant 52. Points having both an X axis value and a Y axis value lower than the first reference value and the second reference value respectively fall into the third quadrant 53. Points having an X axis value equal to or greater than the first reference value and a Y axis value lower than the second reference value fall into the fourth quadrant 54.

For example, the first quadrant 51 is a region in which a point is likely to be plotted when the subject is in a distracted state due to a stimulus such as pain. The second quadrant 52 is a region in which a point is likely to be plotted when the subject is attentive. The third quadrant 53 is a region in which a point is likely to be plotted when the subject is focused. The difference between "attentive" and "focused" is that "attentive" describes a state in which the subject pays attention to their surroundings while still managing input, processing, and output of information focused on required objectives, whereas "focused" describes a state in which the subject devotes their attention continuously to a single task. The fourth quadrant 54 is a region in which a point is likely to be plotted when the subject is distracted due to sleepiness or the like. By establishing in advance the characteristics associated with each quadrant in this manner, the subject state can be inferred based on which quadrant a point is plotted in.

By looking only at points plotted in a specific quadrant out of the first quadrant 51 to the fourth quadrant 54, it is possible to clearly infer the type and level of the subject state, as well as the time when the subject entered this state. Explanation follows regarding looking at a specific quadrant.

Figure 7:
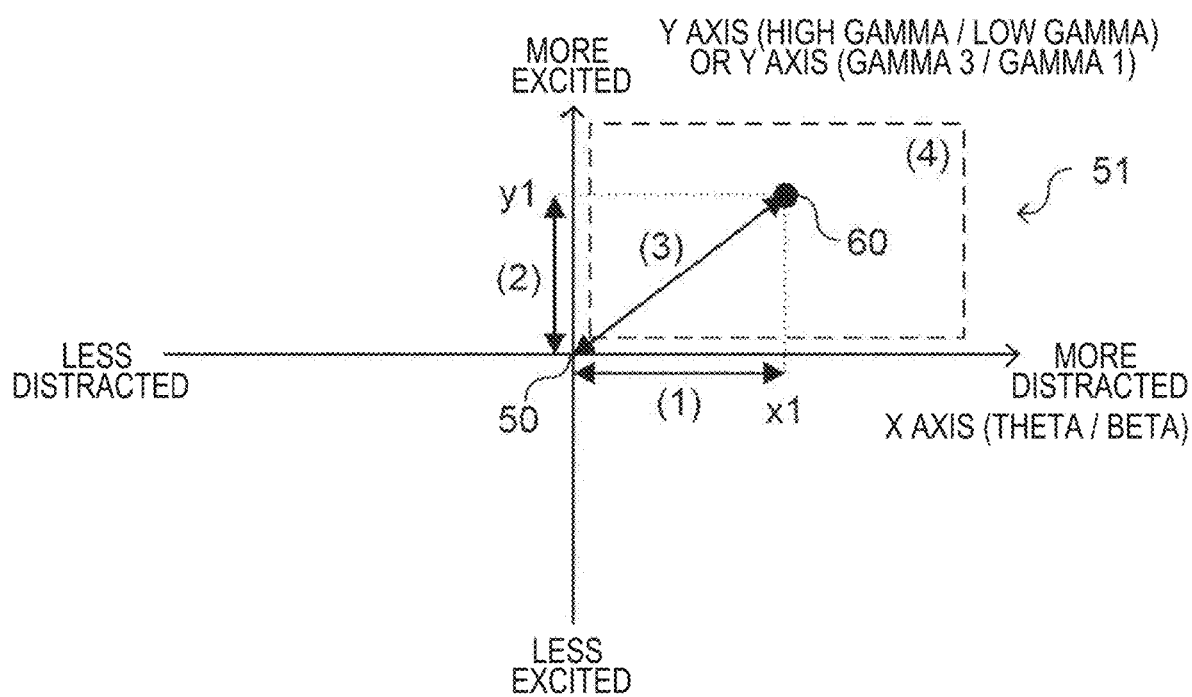
FIG. 7 is a diagram illustrating a theory regarding index values of points on a coordinate system.
Figure 8:
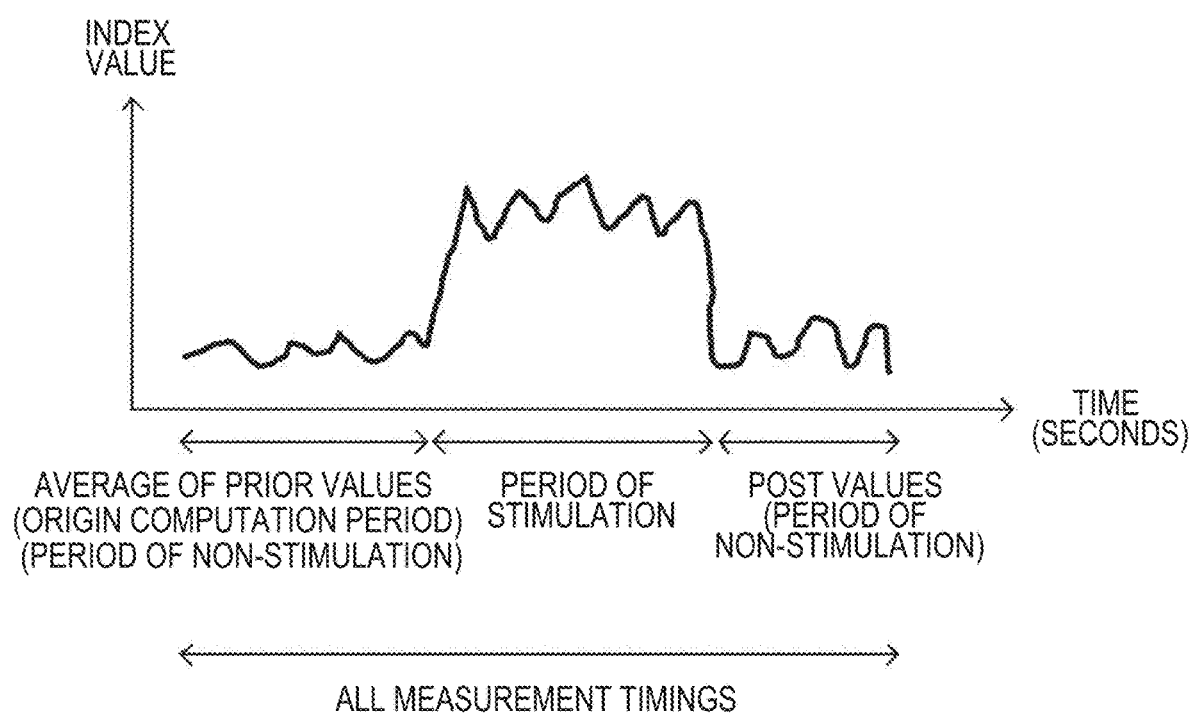
FIG. 8 is a diagram illustrating transition over time of index values.

FIG. 7 is a diagram illustrating a theory of index values for points in the coordinate system. FIG. 8 is a diagram illustrating transition over time of index values.

FIG. 7 illustrates an example looking at the first quadrant 51. When a point 60 has been plotted in the first quadrant 51, it is possible to take the five values below as index values.

Index value A: X axis direction distance to point 60 from origin 50 (x1)

Index value B: Y axis direction distance to point 60 from origin 50 (y1)

Index value C: distance to point 60 from origin 50 $((x1^2+y1^2)^{1/2})$ Index value D: appearance frequency of points plotted (appearing) in first quadrant 51

Index value E: product of D and any of A to C

This is not limited to the first quadrant 51, and similarly index values may be obtained based on the relationship to the origin 50 and the appearance frequency of points in each quadrant for points plotted in the second quadrant 52 to the fourth quadrant 54.

By employing any of the above index values A to E, a graph such as that illustrated in the example of FIG. 8 can be obtained by arranging the transition over time of the index values in time sequence.

From the graph illustrated in FIG. 8, it can be seen that the index values are greater during a period of stimulation in which the subject is stimulated than in periods before and after the period of stimulation. By expressing the transition over time of the index values in time sequence in this manner, changes in the subject state can be seen clearly, enabling a clear inference of a specific state. The size of the index values further enables the level of the specific state, for example the level of focus, to be inferred.

Note that in the example illustrated in FIG. 8, the period prior to stimulation is designated an origin computation period, and after finding averages of the first ratio and the second ratio computed from the brain waves in the origin computation period as the origin in FIG. 7, the index values such as the aforementioned index values A to E are found and these index values are used to express change over time. In FIG. 8, a clear spike can be seen in the index values during the period of stimulation in comparison to the index values in the period prior to stimulation. As this demonstrates, it is important which period of brain waves to use when computing the first reference value and the second reference value that are used to infer the subject state. Instead of a period prior to the period of stimulation in which stimulation is applied, the origin computation period may be any out of the period of stimulation, a period after the period of stimulation, a period of non-stimulation (a period between periods of stimulation), or a full period spanning from a period prior to the period of stimulation to a period after the period of stimulation. Alternatively, the first reference value and the second reference value may be calculated in real time on a continuous basis instead of being computed after performing brain wave measurement. In such cases, the brain wave analysis device 30 transmits the brain wave data on a continuous basis and the first reference value and the second reference value are updated in a received range. This enables sudden changes in the subject state to be identified and the state to be inferred.

Note that in the present exemplary embodiment, at step S105, the coordinate system is created and the subject state is judged based on which quadrant points appear in in the coordinate system. However, the present exemplary embodiment does not necessary rely on the premise of a coordinate system. For example, the subject state may be inferred based on a difference between the first ratio and the first reference value computed by the computation section 301 and a difference between the second ratio and the second reference value computed by the computation section 301. In such cases, the subject state may be inferred by determining for the first ratio and the second ratio as computed by the computation section 301 whether the first ratio is equal to or greater than the first reference value and the second ratio is equal to the second reference value, the first ratio is equal to or greater than the first reference value and the second ratio is lower than the second reference value, the first ratio is lower than the first reference value and the second ratio is equal to or greater than the second reference value, or the first ratio is lower than the first reference value and the second ratio is lower than the second reference value.

Next, explanation follows regarding Examples.

Example 1

Figure 9:
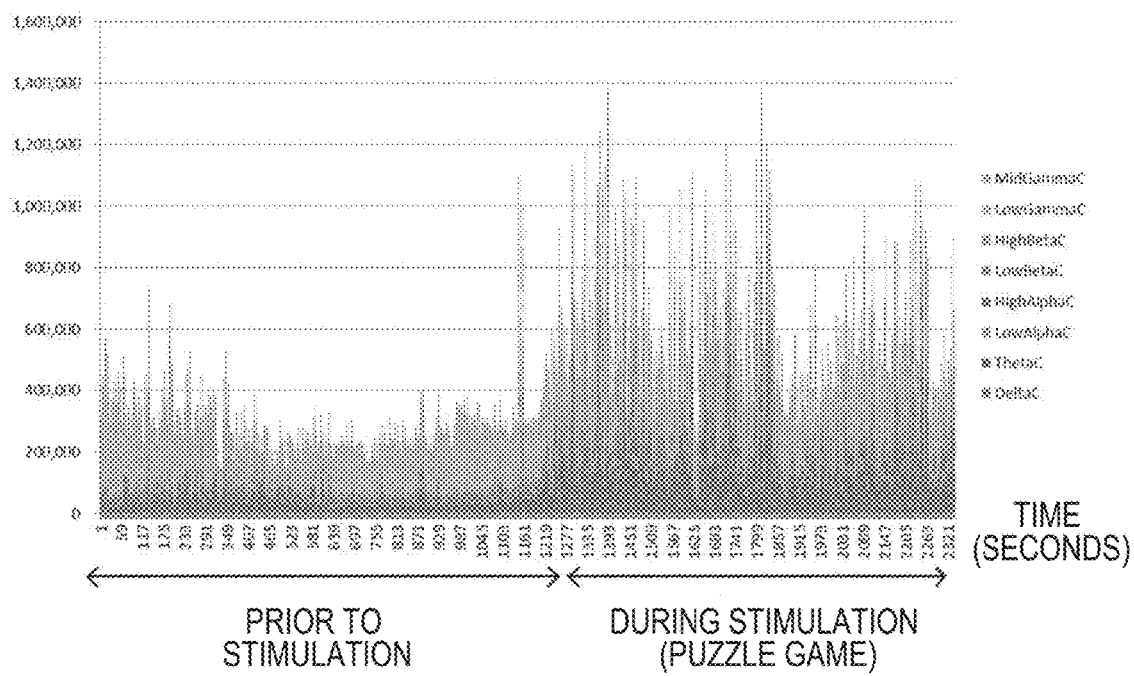
FIG. 9 is a diagram illustrating transition over time of an amplitude spectrum during a measurement period.
Figure 10:
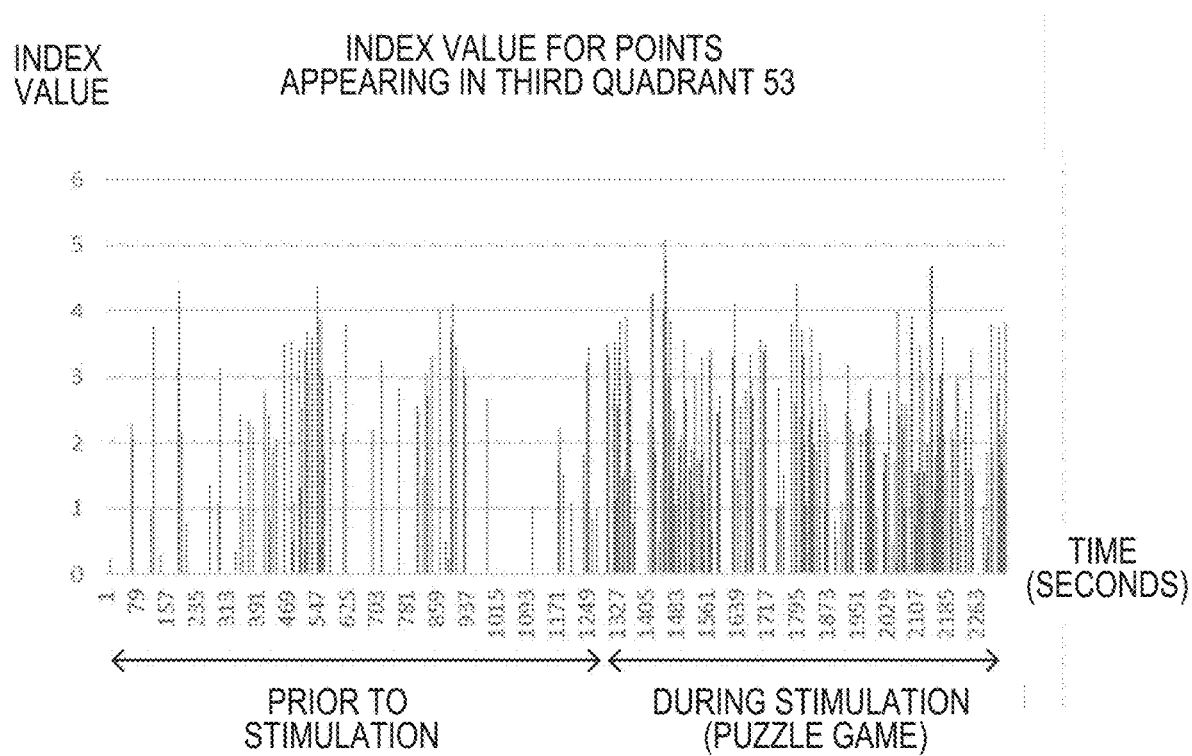
FIG. 10 is a diagram illustrating transition over time of index values for points appearing in a third quadrant in FIG. 6.
Figure 11:
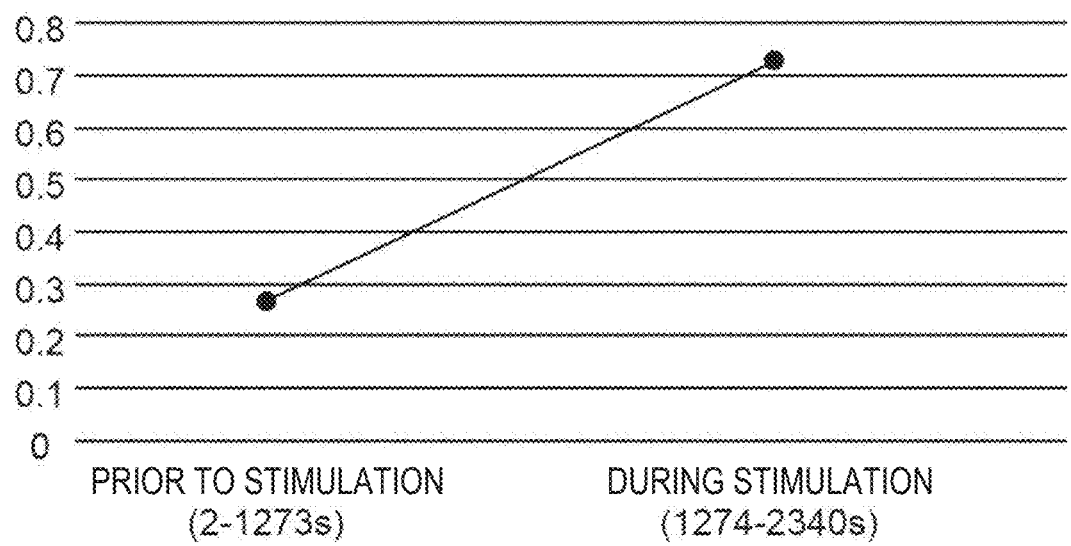
FIG. 11 is a diagram illustrating averages of index values before and during stimulation.

FIG. 9 is a diagram illustrating transition over time of an amplitude spectrum during a measurement period. FIG. 10 is a diagram illustrating transition over time of index values for points appearing in the third quadrant 53 of FIG. 6. FIG. 11 is a diagram illustrating averages of the product of distance from the origin and appearance frequency in the third quadrant 53 both prior to stimulation and during stimulation.

In Example 1, brain waves of the subject were detected by the data acquisition section 10 for approximately 40 minutes. The subject was made to perform a puzzle game from approximately 20 minutes into the brain wave detection until the end of the brain wave detection so as to stimulate the subject.

After brain wave detection ended, the brain wave data was transmitted from the data acquisition section 10 to the brain wave analysis device 30, and the brain waves were analyzed by the brain wave analysis device 30. This brain wave analysis was performed according to the brain wave analysis processing illustrated in FIG. 5. When creating a coordinate system at step S105, brain wave data spanning the entire subject measurement period was employed to create the coordinate system, having the first reference value and the second reference value, configured by averages of the brain wave data, at the origin. At step S106, the third quadrant 53 of the coordinate system illustrated in FIG. 6 was considered, and index values were only computed for points appearing in the third quadrant 53. The index values were computed as the distances to these points from the origin 50.

The results illustrated in FIG. 9 were obtained for the transition over time of an amplitude spectrum of the brain waves as a result of analysis under the conditions described above. All wave amplitudes obtained by the Fourier transform are illustrated in the results in FIG. 9. It can be seen that the amplitudes of some waves increased when the subject performed the puzzle game. It is difficult to see which waves experienced an increase in amplitude. Note that the data for the transition over time of the amplitude spectrum illustrated in FIG. 9 includes noise caused by a power source. Such noise caused by the power source is referred to hereafter as power source noise. The power source noise is preferably removed. When removing such power source noise, the frequency of a commercial power supply (either 50 Hz or 60 Hz in the case of Japan) or, in cases in which an inverter is nearby, the frequency after transformation, is removed. The power source noise is removed by cutting out a range with the corresponding frequency as a median value. This range may be adjusted according to the power source noise intensity. In cases in which the power source noise is intense, a frequency band with a wider range with respect to the median value is removed than in cases in which the power source noise has low intensity. For example, in a case in which the commercial power supply frequency is 50 Hz, a frequency band corresponding to a range of from 49.25 Hz to 50.75 Hz may be removed from the amplitude spectrum. The range to be cut may be set to from 0.25 Hz to several Hz on either side of the median value.

The results illustrated in FIG. 10 are obtained by creating the coordinate system illustrated in FIG. 6 and computing the index values for the points appearing in the third quadrant 53. Since points tend to appear in the third quadrant 53 when the subject is focused, as illustrated in FIG. 10, the index values appear with higher frequency when stimulated by the puzzle game than prior to stimulation. Namely, it can be seen that when the subject is performing the puzzle game, points appear in the third quadrant 53 in the coordinate system illustrated in FIG. 6 with high frequency. It can also be seen that these index values are somewhat higher when stimulated.

In both the period prior to stimulation and the period of stimulation, averages of the index values (distance from the origin) of the points that appear are multiplied by the frequency with which the points appear. By so doing, as illustrated in FIG. 11, it can be seen that a value that is no greater than 0.3 prior to stimulation becomes 0.7 or greater during stimulation, representing an increase of at least double. In this manner, it can be seen that expressing the state in numerical form using the index values for each period enables changes in the subject state to be clearly and quantitatively expressed.

Example 2

Figure 12:
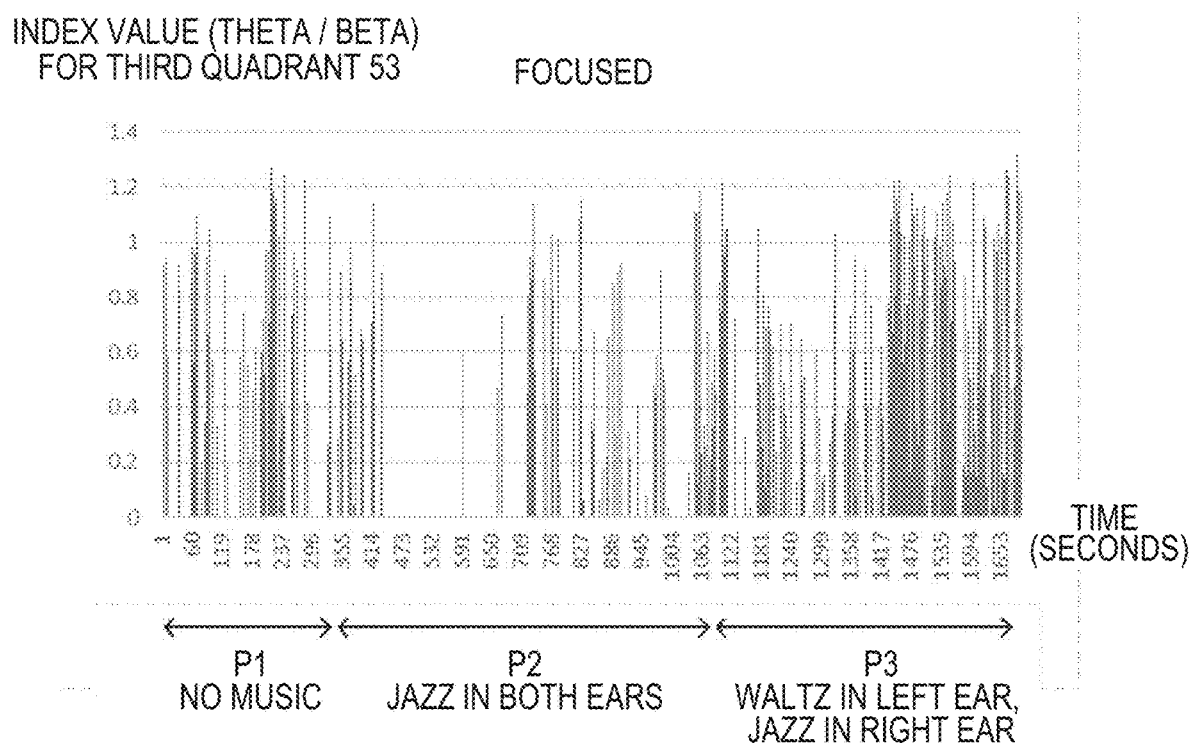
FIG. 12 is a diagram illustrating transition over time of index values for points appearing in the third quadrant in FIG. 6.
Figure 13:
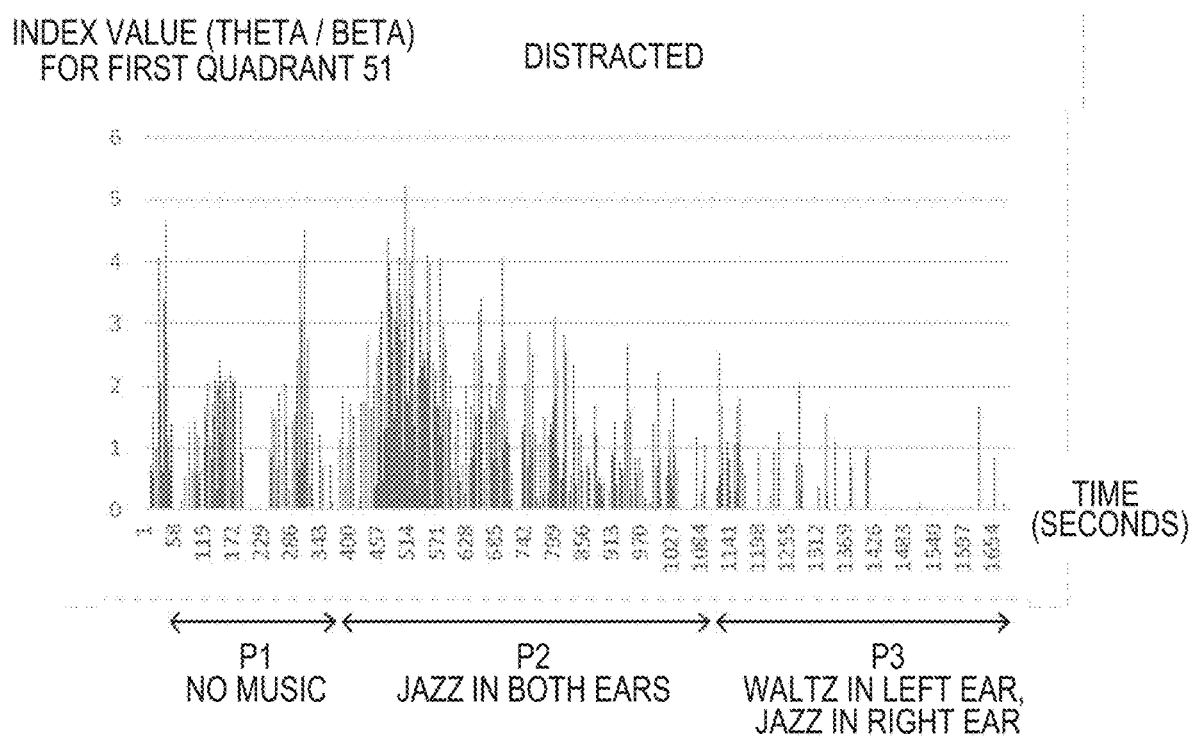
FIG. 13 is a diagram illustrating transition over time of index values of points appearing in a first quadrant in FIG. 6.

FIG. 12 is a diagram illustrating transition over time of index values for points appearing in the third quadrant in FIG. 6. FIG. 13 is a diagram illustrating transition over time of index values for points appearing in the first quadrant in FIG. 6.

In Example 2, headphones were placed over both ears of the subject and brain waves were measured for approximately 27 minutes. The brain wave measurement period included a period P1 in which no music was played at all, a period P2 in which jazz music was played into both ears of the subject through the headphones, and a period P3 in which waltz music was played into the left ear of the subject and jazz music was played into the right ear of the subject through the headphones. The period P1 lasted approximately 5 minutes, the period P2 lasted approximately 11 minutes, and the period P3 lasted approximately 11 minutes.

After brain wave detection ended, the brain wave data was transmitted from the data acquisition section 10 to the brain wave analysis device 30, and the brain waves were analyzed by the brain wave analysis device 30. This brain wave analysis was performed according to the brain wave analysis processing illustrated in FIG. 5. When creating a coordinate system at step S105, brain wave data for all measurement timings was employed to create the coordinate system, having the first reference value and the second reference value, configured by averages of the brain wave data, at the origin. At step S106, the first quadrant 51 and the third quadrant 53 of the coordinate system illustrated in FIG. 6 were considered, and index values were computed for points appearing in the first quadrant 51 and the third quadrant 53. The index values were computed as the X axis direction distances to these points from the origin 50.

FIG. 12 and FIG. 13 illustrate transition over time of the index values obtained as a result of the analysis under the conditions described above.

FIG. 12 illustrates index values for points appearing in the third quadrant 53. Points tend to appear in the third quadrant 53 in cases in which the subject is focused. It can be seen that the frequency with which points appeared during the second period P2 during which jazz music was played into both ears was lower than during the first period P1 during which music was not played. It can also be seen that the frequency with which points appeared during the third period P3 during which different music was played into each ear was greater than during the first period P1.

FIG. 13 illustrates index values for points appearing in the first quadrant 51. Points tend to appear in the first quadrant 51 in cases in which the subject is in a distracted state. It can be seen that the frequency with which points appeared during the second period P2 during which jazz music was played into both ears was greater than during the first period P1 during which music was not played. It can also be seen that the frequency with which points appeared during the third period P3 during which different music was played into each ear was lower than during the first period P1.

As described above, FIG. 12 and FIG. 13 illustrate a contrasting focused state and distracted state, and it can be seen that the frequency with which points appeared reversed between the period P2 and the period P3. This lends credibility to the theory that a focused state of the subject can be inferred by looking at the first quadrant 51 and that a distracted state of the subject can be inferred by looking at the third quadrant 53.

Example 3

Figure 14:
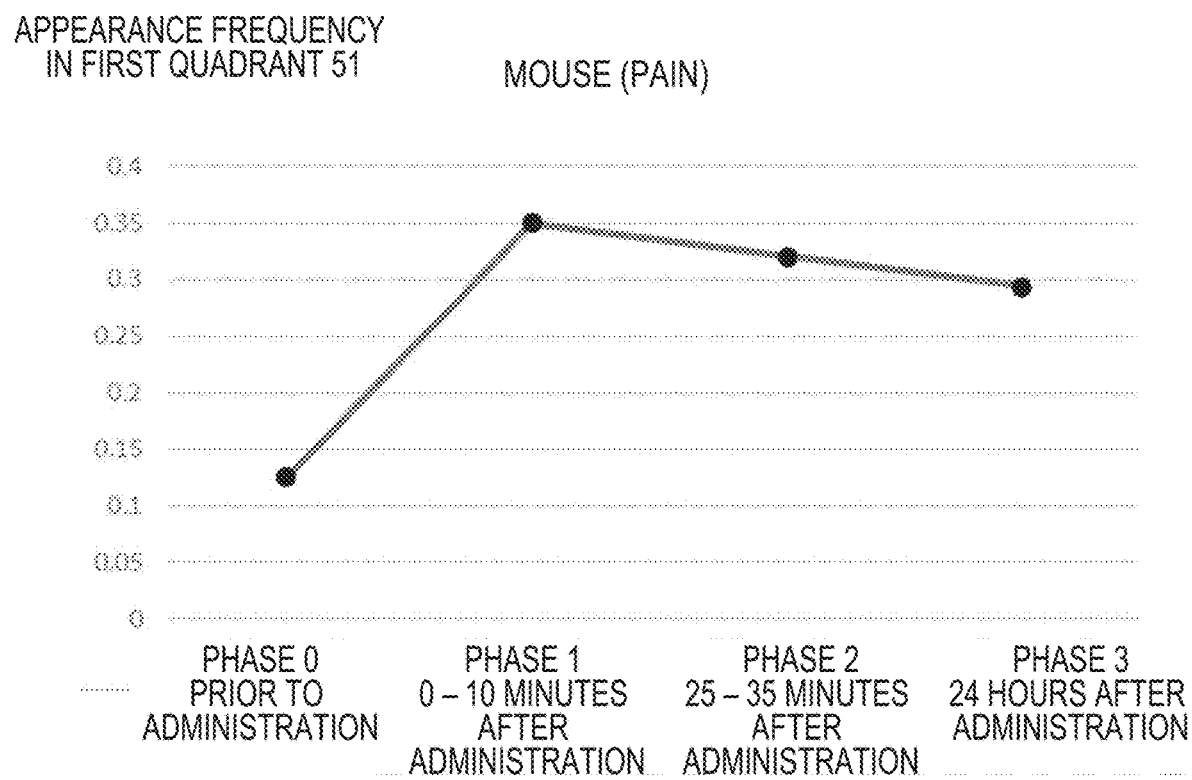
FIG. 14 is a diagram illustrating test results for pain, using a mouse.

FIG. 14 illustrates test results for pain, using a mouse.

In Example 3, a mouse was used to verify inference of the subject state based on the brain wave analysis processing described above.

First, a brain stereotaxic instrument was fixed to the mouse anaesthetized using isoflurane, and the tips of tungsten electrodes were positioned by being implanted and fixed in the primary somatosensory cortex, the habenular nuclei, and the prefrontal cortex. From five days after this surgery, localized electric field potential from the mouse during free activity in an open field was recorded (using an RZ5 manufactured by Tucker-Davis Technologies as the recording instrument). 20 μL of a 5% formalin solution was then subcutaneously injected into the back of the rear left leg, and the localized electric field potential was again recorded for one hour of free activity in an open field. Further, 24 hours after administration, the localized electric field potential from the mouse during one hour of free activity in an open field was again recorded. The total time spent engaged in pain behavior such as licking or biting of the leg was measured by sight using a stopwatch as pain behavior evaluation following administration of the formalin.

Frequency spectrum analysis of the localized electric field potential from the prefrontal cortex was performed and respective frequency bands were separated in order to judge the level of brain activity based on the strength of these frequency bands. The frequency data was analyzed for four time points, namely prior to formalin administration, 0 to 10 minutes after administration (referred to as Phase 1 or P1), 25 to 30 minutes after administration (referred to as Phase 2 or P2), and for 10 minutes 24 hours after administration. Further, analysis was performed for two time points after the formalin administration, namely from 0 to 5 minutes after administration (referred to as PF) and from 10 to 15 minutes after administration (referred to as P1-2).

The results based on these brain waves are as illustrated in FIG. 14. FIG. 14 illustrates the frequency with which data (points) were plotted in the first quadrant 51 when having averages for all brain wave measurement timings at the X axis and the Y axis origin, namely as the first reference value and the second reference value. As illustrated in FIG. 14, there was a marked increase in the appearance frequency with which points appeared in the first quadrant 51 based on the brain waves in Phases 1 to 3 than in a Phase 0 prior to formalin administration. The appearance frequency with which points appeared in the first quadrant 51 gradually decreased over time on progression from Phase 1 to Phase 3.

The transition over time of the frequency with which points appeared in the first quadrant 51 was consistent with the transition over time of the total time spent engaged in pain behavior as observed visually. It could be confirmed from this that the changes in the mouse state as inferred from the brain waves conformed to actual changes in the mouse state.

Myoelectric Noise Cancellation

Figure 15:
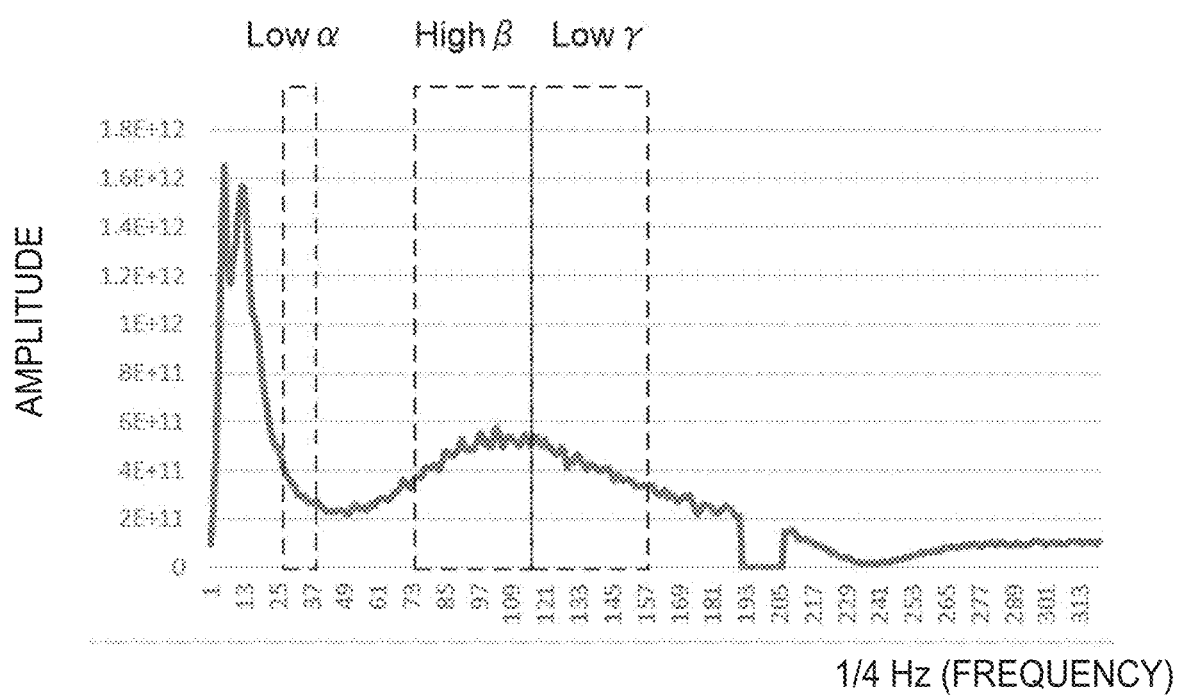
FIG. 15 is a diagram illustrating an example of an amplitude spectrum obtained by performing frequency analysis on brain waves of a subject.
Figure 16:
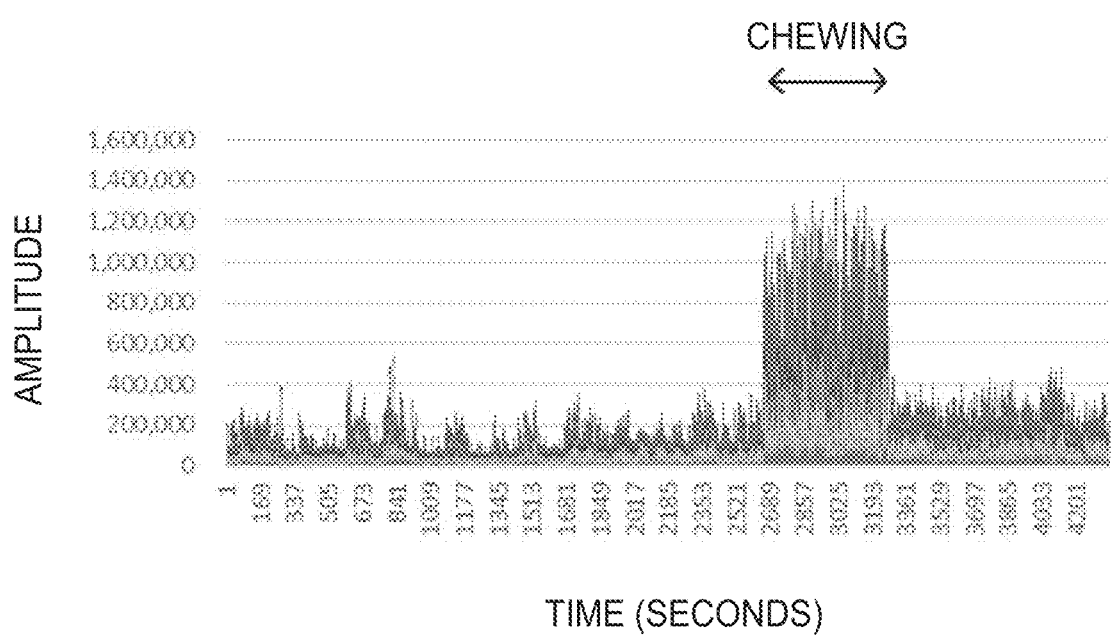
FIG. 16 is a diagram illustrating transition over time of an amplitude spectrum during a measurement period.
Figure 17:
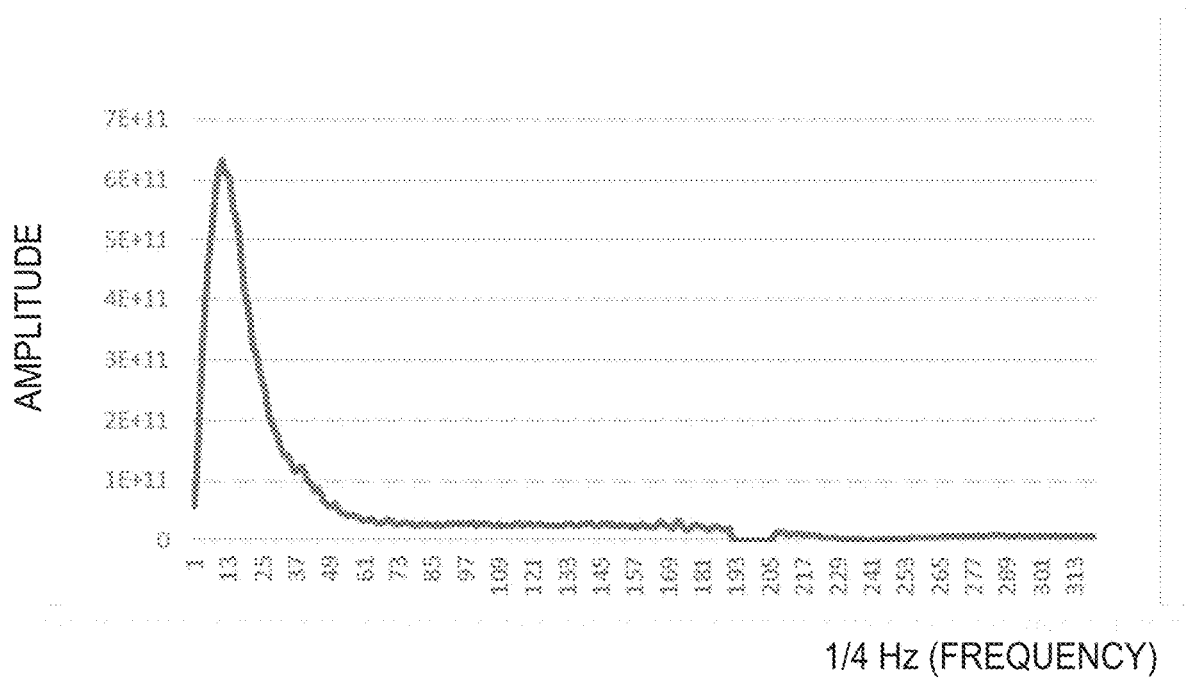
FIG. 17 is a diagram illustrating an example of an amplitude spectrum after noise removal.
Figure 18:
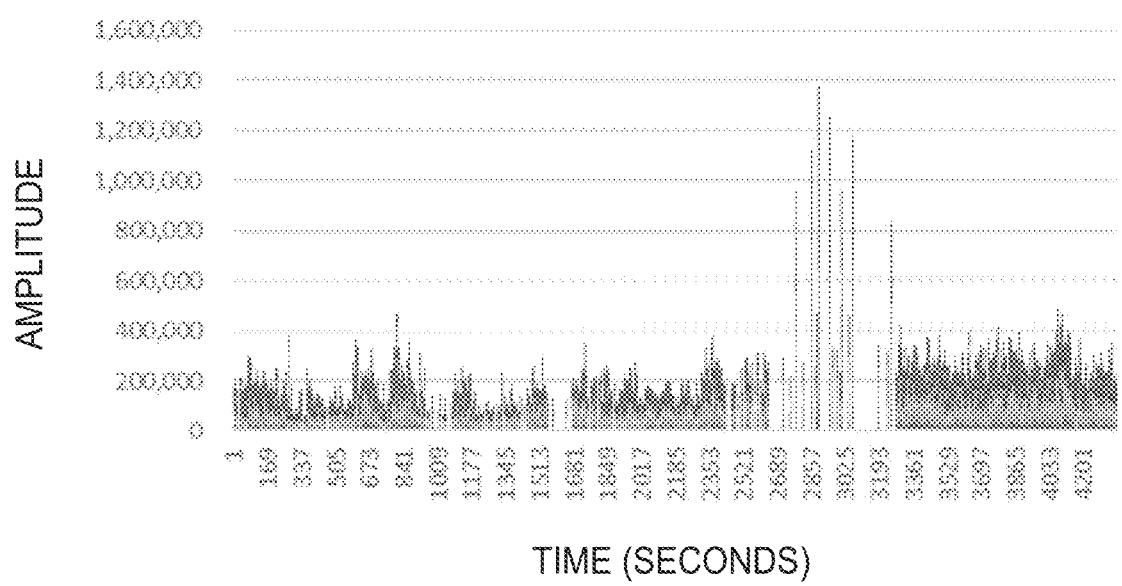
FIG. 18 is a diagram illustrating transition over time of an amplitude spectrum after noise removal.

FIG. 15 is a diagram illustrating an example of an amplitude spectrum obtained by brain wave frequency analysis of the subject. FIG. 16 is a diagram illustrating transition over time in the amplitude spectrum over the measurement period. FIG. 17 is a diagram illustrating an example of an amplitude spectrum after noise removal. FIG. 18 is a diagram illustrating the transition over time of the amplitude spectrum after noise removal. Note that in FIG. 15 and FIG. 17, the horizontal axis unit is ¼ Hz, such that, for example, 60 on the horizontal axis corresponds to 15 Hz. In FIG. 15 and FIG. 16, data from a frequency band in the vicinity of 50 Hz and including 50 Hz is removed from the amplitude spectrum data in order to remove power source noise. Explanation follows regarding the removal of myoelectric noise in addition to power source noise.

Explanation follows regarding removal of noise during measurement in the brain wave analysis processing described above. FIG. 17 is a diagram illustrating an amplitude spectrum after noise removal. FIG. 18 is a diagram illustrating transition over time in an amplitude spectrum after noise removal.

When brain waves are measured while going about daily life, action potential arising due to muscle contraction, and in particular potential when chewing, has a major noise effect on brain wave measurement from the frontal region of the head. In order to remove such noise, data having a frequency ratio resembling that of myoelectricity observed when biting down is removed.

According to pages 872 to 888 of Volume 32 Issue 4 of the Pediatric Dental Journal (1994), an electromyogram taken when biting down reveals a substantially linear increase in power accompanying an increase in frequency in a frequency band of at least 0 Hz to 50 Hz (sometimes as wide as 0 Hz to 100 Hz). This overlaps with a frequency band from delta waves to gamma waves in human brain waves, which manifests as noise during brain wave measurement in everyday life using wearable apparatus due to the strong myoelectricity masking brain waves. As the frequency increases and the strength also increases, such data may be omitted from analysis in order to cancel out non-brain wave noise and improve the precision of analysis. For example, cases in which high beta/low alpha>2, and likewise cases in which low gamma/low alpha>2, may be considered to be myoelectricity rather than brain waves, and accordingly thought of as being outside the analysis. Note that although 2 is employed as a reference value (third reference value) in this example, this reference value is not limited to 2. This reference value may be varied according to the specifications of the electroencephalograph employed and so on. Note that the vertical axis of a graph in the literature referred is a percentage scale with respect to the total integral of power values for each of 20 Hz increments.

FIG. 15 illustrates an amplitude spectrum obtained when brain waves of a subject when chewing are acquired by the data acquisition section 10 and subjected to frequency analysis. In this example, distorted waves thought to be due to noise can be observed in the frequency bands of low alpha, high beta, and low gamma waves. FIG. 16 illustrates an example of transition over time of the amplitude spectrum in a specific measurement period including a period in which the subject was chewing. It can be seen that the amplitude increases during the period when the subject was chewing.

The results illustrated in FIG. 17 and FIG. 18 were obtained by removing noise components satisfying at least one out of high beta/low alpha>2 or low gamma/low alpha>2 as described above.

In the amplitude spectrum illustrated in FIG. 17, it can be seen that the distorted waves disappear after removing the chewing noise component. In the transition over time of the amplitude spectrum illustrated in FIG. 18, it can be seen that data from the chewing period during which chewing resulted in an abnormally large amplitude has been substantially removed.

The wave classifications illustrated in FIG. 2 and discussed previously may be generalized as follows. The portion of a third ratio that exceeds the third reference value is regarded as a noise component, the third ratio being a ratio of the amplitude of either a wave in the first frequency band or a wave in the second frequency band with respect to the amplitude of a wave in the fourth frequency band of lower frequency than the second frequency band and higher frequency than the third frequency band. Removing this noise component from the amplitude spectrum enables analysis results for brain waves to be obtained with the noise removed.

The CPU 31 may create a coordinate system in which an average of the value of the first ratio and a value of the second ratio computed from brain waves during a period in which the subject has closed their eyes and is at rest (during closed-eye rest) is taken as the first reference value and the second reference value.

Figure 19:
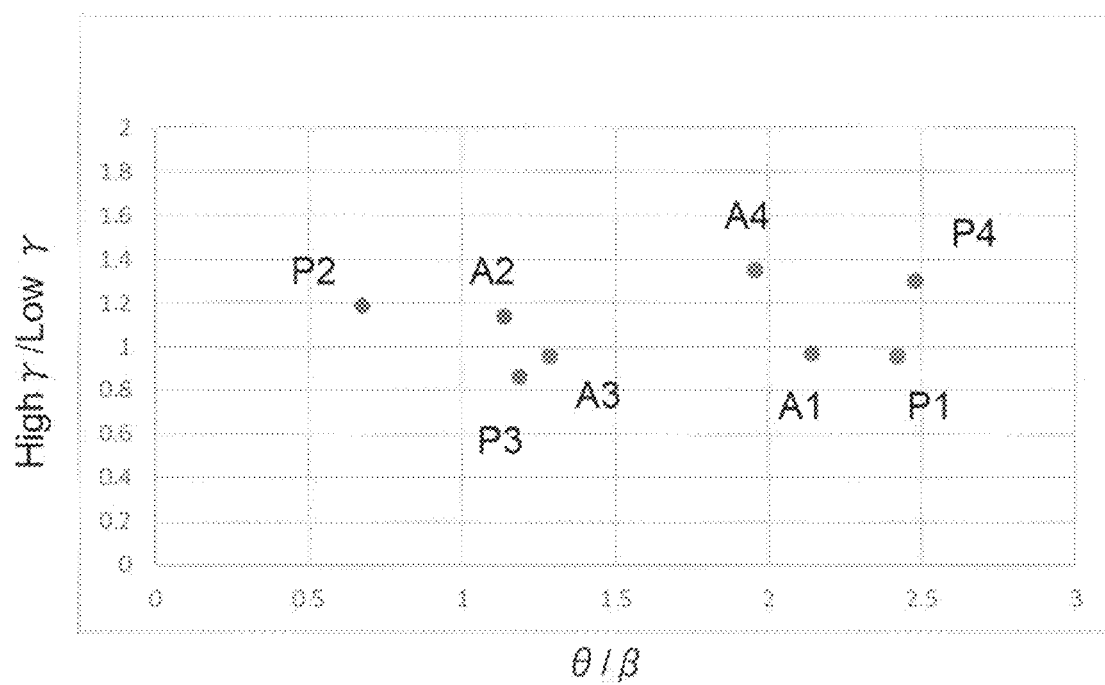
FIG. 19 is a diagram illustrating test results for a human.
Figure 20:
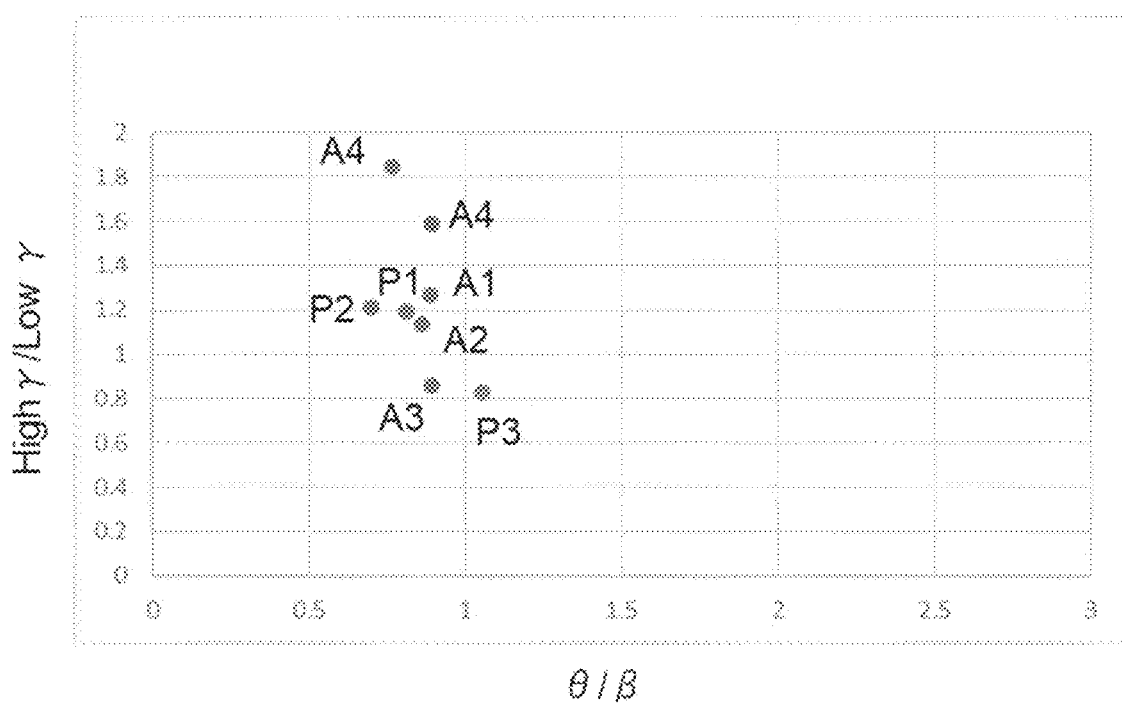
FIG. 20 is a diagram illustrating test results for a human.

FIG. 19 and FIG. 20 are graphs illustrating an example of test results conducted on humans. FIG. 19 is a graph plotted with the first ratio and the second ratio computed from brain wave frequency characteristics in a case in which four human subjects are listening to music in a relaxed state. FIG. 20 is a graph plotted with the first ratio and the second ratio computed from brain wave frequency characteristics in a case in which four human subjects are in a closed-eye resting state. The tests illustrated in FIG. 19 and FIG. 20 were conducted on four human subjects, with a total of two brain waves measurements being performed, in the morning and afternoon respectively. In FIG. 19 and FIG. 20, for example A1 represents plots based on morning measurement results for a first subject, and P1 represents plots based on afternoon measurement results for the same first subject.

As illustrated in FIG. 19 and FIG. 20, the values of the first ratio and the values of the second ratio during closed-eye rest tend to be lower than those when in a relaxed state. Accordingly, when the values for closed-eye rest are adopted at the origin in a coordinate system, the amount of data in the second quadrant 52 and the third quadrant 53 decreases, and it may become difficult to infer whether the subject was attentive or focused.

Accordingly, in a coordinate system in which values for closed-eye rest are adopted at the origin, the CPU 31 may adopt a value obtained by subtracting the appearance frequency in the first quadrant 51 during a period of stimulation from 1 as an index for the level of focus of the subject, and infer the subject state on this basis. In a coordinate system in which values for closed-eye rest are adopted at the origin, such a value obtained by subtracting the appearance frequency in the first quadrant 51 during a period of stimulation from 1 may also be referred to as a distraction reduction factor.

Figure 21:
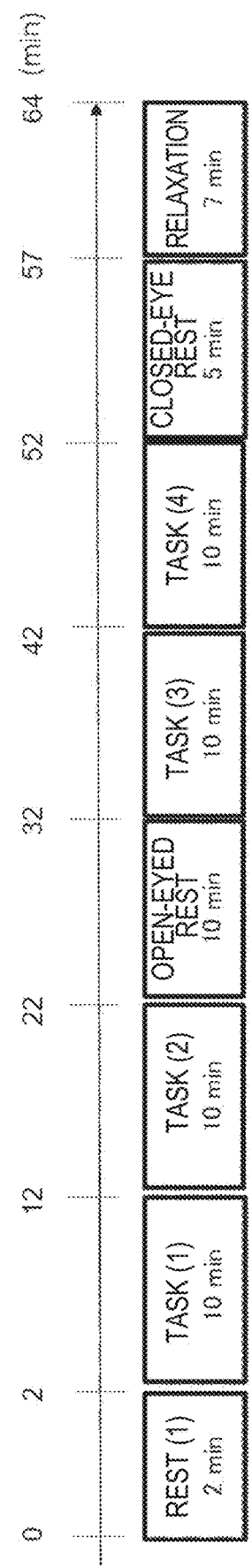
FIG. 21 is a diagram illustrating a sequence during human testing.

Explanation follows regarding an example in which a subject is made to perform tasks in the sequence illustrated in FIG. 21. The subject carries out the respective tasks in an open-eyed state unless otherwise instructed. Rest (1) corresponds to a period in which the subject performs a task that can be performed without being particularly focused or attentive, for example logging onto or restarting a personal computer. Task (1) corresponds to a period in which, for example, the subject performs a task of solving a number-based puzzle set with a fairly unchallenging level of difficulty. Task (2) corresponds to a period in which, for example, the subject performs a task of solving various puzzles within a time limit. Open-eyed rest corresponds to a period in which the subject has their eyes open and disengages as far as possible. Task (3) corresponds to a period in which, for example, the subject performs a task of solving a number-based puzzle set with a more challenging level of difficulty than Task (1). Task (4) corresponds to a period in which, for example, the subject performs a task of solving various puzzles, different to the puzzles of Task (2), within a time limit. Closed-eye rest corresponds to a period in which the subject has their eyes closed and rests as far as possible. Relaxation corresponds to a period in which the subject relaxes while listening to a calming music genre.

Figure 22:
FIG. 22 is a diagram illustrating a frequency with which points appeared in a first quadrant when performing the respective tasks illustrated in FIG. 21 during testing.
Figure 23:
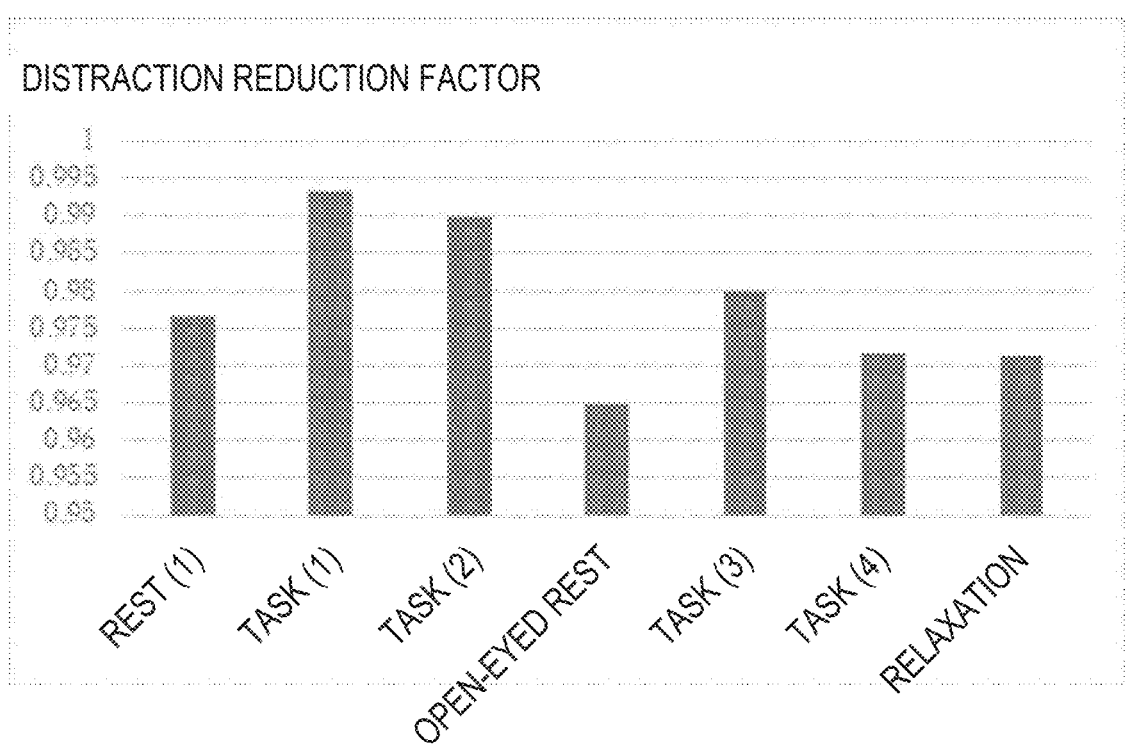
FIG. 23 is a diagram illustrating a distraction reduction factor obtained based on the frequency illustrated in FIG. 22.

FIG. 22 illustrates a polygonal line graph of the appearance frequency in the first quadrant 51 when performing the respective tasks illustrated in FIG. 21. FIG. 23 is a histogram illustrating the distraction reduction factor (value obtained by subtracting the appearance frequency in the first quadrant 51 during the period of stimulation from 1) when performing the respective tasks illustrated in FIG. 21. In the histogram in FIG. 23, a greater bar height indicates a greater level of focus of the subject. Accordingly, the CPU 31 may infer the subject state using the distraction reduction factor for the subject.

Although the coordinate system is created using the second ratio as the horizontal axis in the present exemplary embodiment, examples of the present invention are not limited thereto. Instead of using the second ratio, a coordinate system may be created by splitting a frequency band equal to or greater than the third frequency band generated during a sleeping state or the like and lower than the second frequency band generated in an awake state, by splitting into two and plotting feature values obtained from the wave strengths of each resulting band on the horizontal axis. Namely, in the case of a human, the third frequency band and the fourth frequency band, the third frequency band and the fourth frequency band (3.5 Hz to 11.75 Hz) for example being generated in a light sleeping state, may be split into two to create a coordinate system employing feature values obtained from the wave strengths of the resulting bands as the horizontal axis. Alternatively, in the case of a mouse, the third frequency band (4 Hz to 12 Hz) may be split in two to create a coordinate system employing feature values obtained from the wave strengths of the resulting bands as the horizontal axis.

Figure 24:
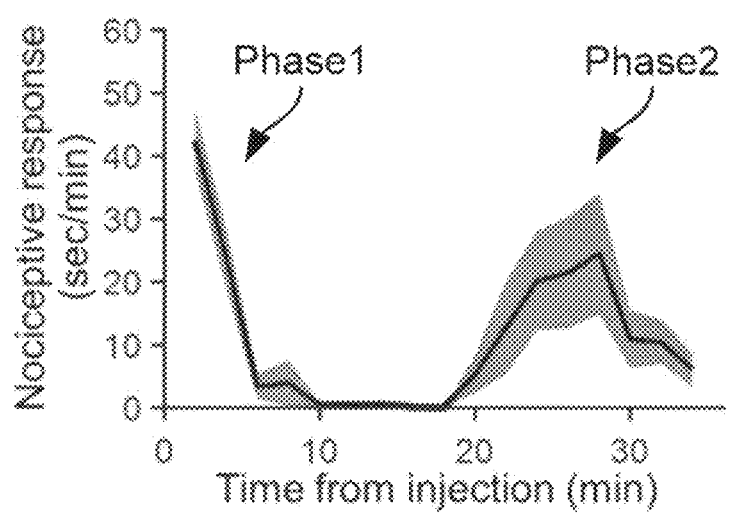
FIG. 24 is a diagram illustrating a relationship between time since formalin administration to a mouse and a nociceptive response in an Example 3.

FIG. 24 is a graph illustrating a relationship between time from formalin administration to a mouse and a nociceptive response in Example 3. As illustrated in FIG. 24, although a nociceptive response was observed in Phase 1 (0 to 10 minutes after administration) and Phase 2 (25 to 35 minutes after administration), almost no nociceptive response was observed during a period between Phase 1 and Phase 2.

Figure 25:
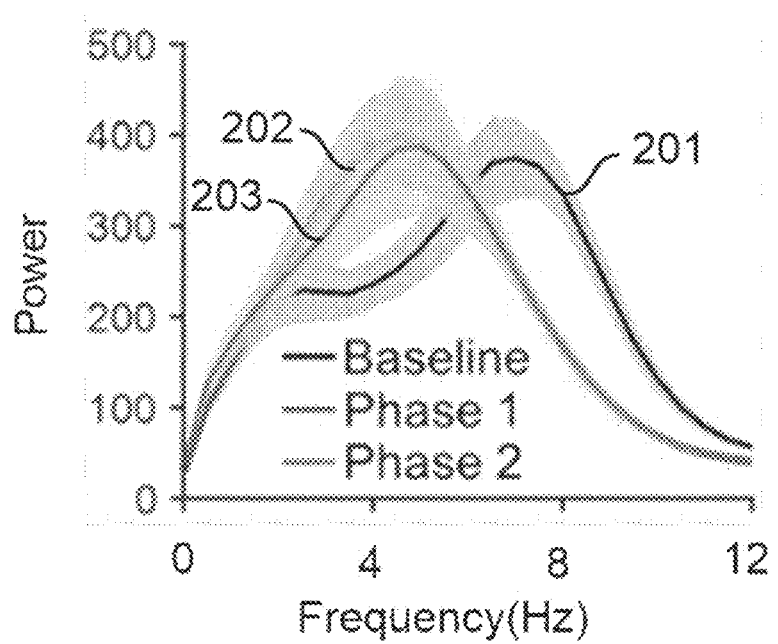
FIG. 25 is a diagram illustrating frequency characteristics in a theta wave frequency band when in pain and when not in pain in Example 3.

FIG. 25 is a graph illustrating frequency characteristics in a theta wave frequency band when in pain and when not in pain in Example 3. Frequency characteristics when not in pain are labeled 201. Frequency characteristics during the Phase 1 period are labeled 202. Frequency characteristics during the Phase 2 period are labeled 203. As illustrated in FIG. 25, the pain test results using a mouse show more of a tendency for the theta wave peak to shift toward the lower frequency side when in pain, namely during Phase 1 and Phase 2, than when not in pain.

Figure 26:
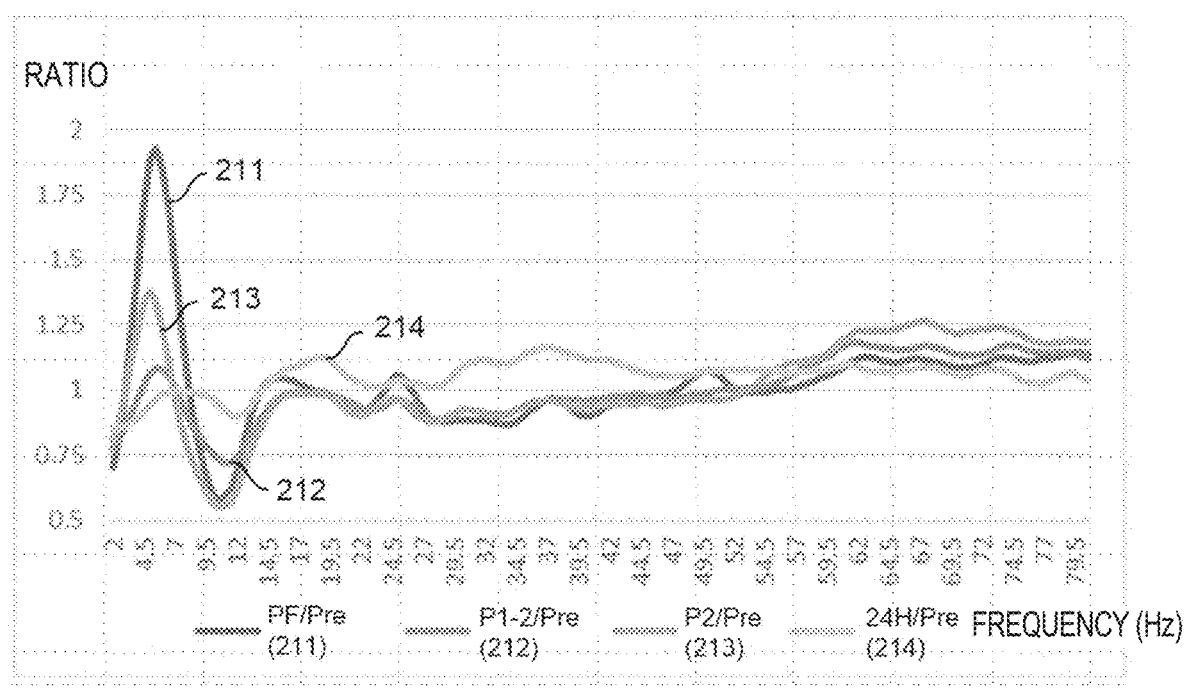
FIG. 26 is a diagram illustrating frequency characteristics of mouse brain wave strength ratios before and after formalin administration to a mouse in Example 3.

FIG. 26 is a graph illustrating frequency characteristics for a ratio of mouse brain wave strength before and after administration for a mouse administered with formalin in Example 3. FIG. 26 illustrates a wave strength ratio for each frequency as measured with respect to the mouse brain wave strength prior to formalin administration (Pre), for 0 to 5 minutes after administration (PF), for 0 to 10 minutes after administration (Phase 1: P1), from 10 to 15 minutes after administration (P1-2), from 25 to 35 minutes after administration (Phase 2: P2), and 24 hours after administration (24 H). Since the period PF is included in the period P1, in the following explanation the period P1 and the period PF are collectively denoted P1 (PF) when relevant to both. The strength ratio during the period P1 (PF) is labeled 211. The frequency characteristics during the period P1-2 are labeled 212. The strength during the P2 is labeled 213. The strength ratio 24 hours after formalin administration is labeled 214.

As illustrated in FIG. 26, the pain test results using a mouse indicate a clear rise in theta wave strength when in pain, namely during P1 (PF) and P2 at around 5 Hz. A strength ratio peak for theta waves when not in pain between P1 (PF) and P2, and a strength ratio peak for theta waves when not in pain 24 hours after administration are smooth, at around 6 Hz to 8 Hz. Namely, a tendency for the theta wave peak when in pain, namely during P1 (PF) and P2 to shift toward the lower frequency side compared to the theta wave peak when not in pain can be observed.

Moreover, as illustrated in FIG. 26, a tendency for the strength ratio to increase was observed in a gamma wave region when in pain, namely during P1 (PF) and P2. Furthermore, as illustrated in FIG. 26, a tendency was observed for the strength ratio in the period (P1-2) between P1 (PF) and P2 to be closer to that when not in pain after 24 hours (24 H/Pre) than in the immediately preceding and following periods. In other words, after administering the formalin to the mouse, a tendency was observed for two pain peaks to appear corresponding to the two timings P1 (PF) and P2 in which the strength ratio for theta waves and gamma waves (60 Hz and above) was greater than when not in pain (24 Hr/Pre).

The tendency for the theta wave peak to shift when in pain will now be considered. The CPU 31 may split the theta wave frequency band into two to create a coordinate system employing a feature value difference obtained from the wave strengths in the resulting bands as a horizontal axis. The feature value difference obtained from the wave strengths in the two bands is defined as a difference amount. The CPU 31 employs an average of the difference amounts for all measurement timings found using an arithmetic mean method, a weighted average method, a root-mean-square method, or the like, an average of a natural logarithm of the difference amounts spanning all brain wave measurement timings, or a median value of the difference amounts as the second reference value.

Figure 27:
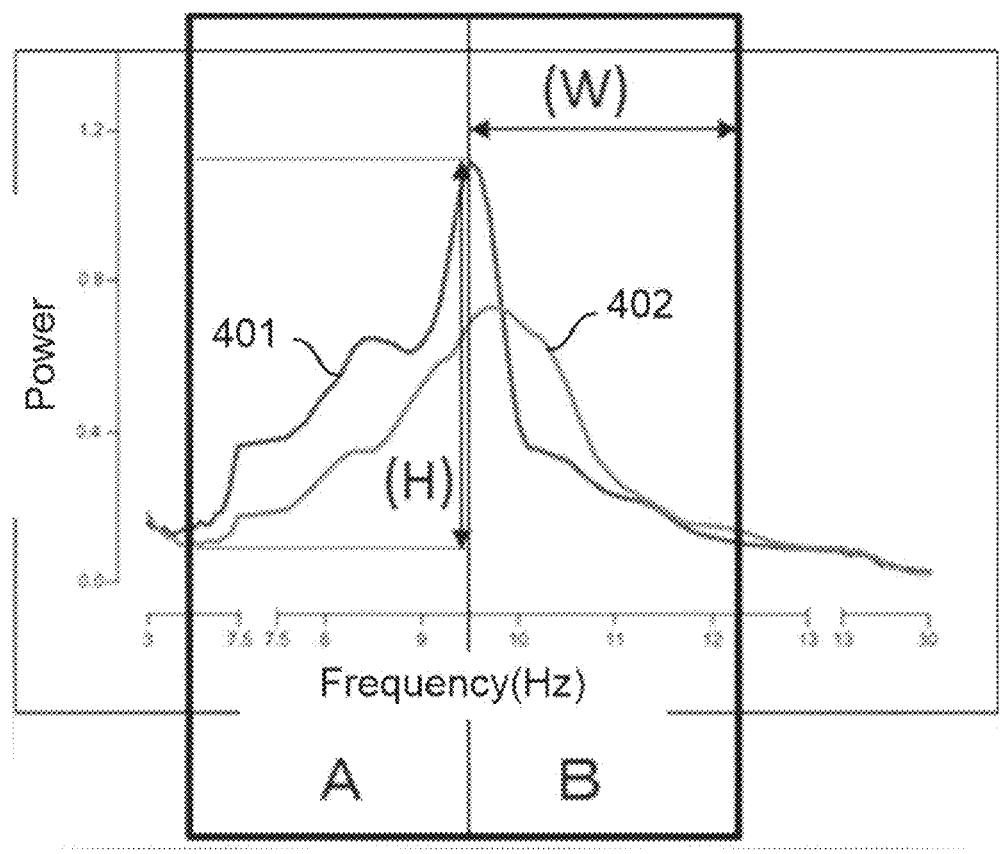
FIG. 27 is a diagram to explain a difference amount between mouse brain wave strength ratios before and after formalin administration to a mouse.
Figure 28:
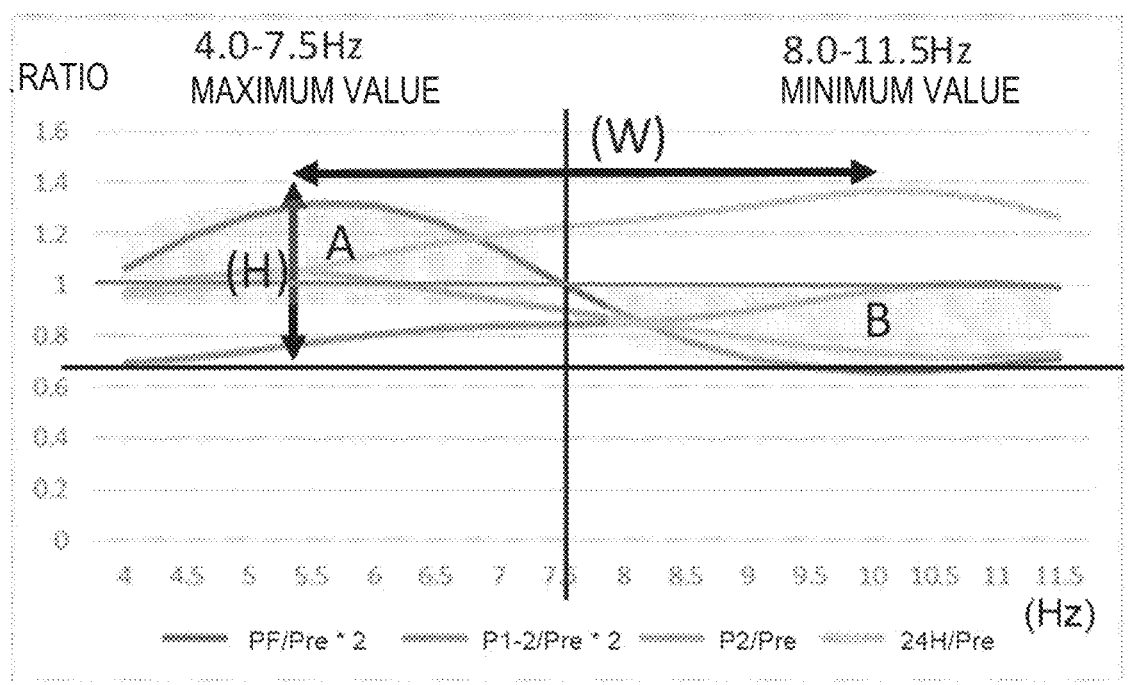
FIG. 28 is a diagram to explain a difference amount between mouse brain wave strength ratios before and after formalin administration to a mouse.
Figure 29:
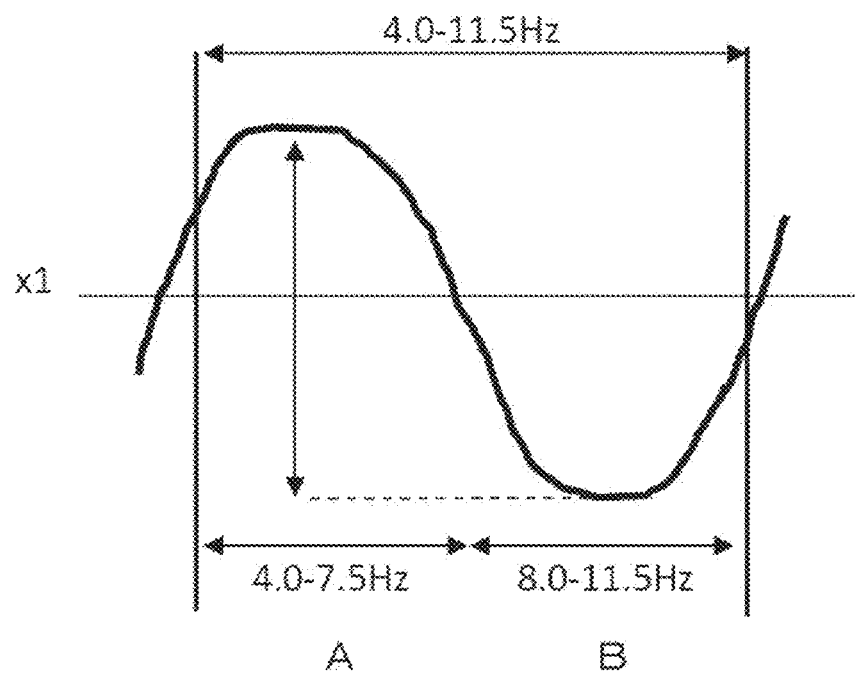
FIG. 29 is a diagram to explain a difference amount between mouse brain wave strength ratios before and after formalin administration to a mouse.

FIG. 27, FIG. 28, and FIG. 29 are graphs for explaining the difference amount of the strength ratio of mouse brain waves before and after administration in the case of a mouse administered with formalin. Various values may be adopted as the difference amount. When a frequency band is split in two, a low frequency side A region and a high frequency side B region are obtained.

FIG. 27 is a graph illustrating frequency characteristics for amplitude strength in the case of human brain waves. Frequency characteristics of brain waves when in pain are labeled 401. Frequency characteristics of brain waves when not in pain are labeled 402. In the example in FIG. 27, the A region corresponds to approximately 4.0 Hz to 9.5 Hz, and the B region corresponds to approximately 9.5 Hz to 12 Hz. FIG. 28 and FIG. 29 are graphs illustrating frequency characteristics of ratios when not in pain in the case of mouse brain waves. In the examples of FIG. 28 and FIG. 29, the A region corresponds to approximately 4.0 Hz to 7.5 Hz, and the B region corresponds to approximately 8.0 Hz to 11.5 Hz. FIG. 29 is a graph in which the frequency characteristics for Phase 1 in the graph in FIG. 28 are plotted in isolation.

Note that although the frequency band is configured by the A region and the B region as described above in the present exemplary embodiment, there is no limit to examples relating to all frequency band regions. For example, in the case of a human, ranges of 1 to 2 Hz on either side of a peak frequency appearing in a high alpha wave to low alpha wave frequency band may configure the A region, and a region on the high frequency side of the A region in the high alpha wave to low alpha wave frequency band may configure the B region. As another example, in the case of a mouse, a theta wave frequency band may be evenly split and the low frequency side configure the A region and the high frequency side configure the B region.

The CPU 31 may employ a maximum power value of the A region as the A region feature value and employ a minimum power value of the B region as the B region feature value. Alternatively, the CPU 31 may employ an amplitude value in the A region as the A region feature value and employ an amplitude value in the B region as the B region feature value. Alternatively, the CPU 31 may employ a power integral value of the A region as the A region feature value and employ an integral of a power value of the B region as the B region feature value. The CPU 31 may also employ a value obtained by subtracting the B region feature value from the A region feature value as the difference amount. In FIG. 27 and FIG. 28, H corresponds to a difference value in a case in which the maximum power value of the A region is employed as the A region feature value and the minimum power value of the B region is employed as the B region feature value.

Alternatively, the CPU 31 may employ the frequency of the maximum peak power value of the A region as the A region feature value and employ the frequency of the minimum peak power value of the B region as the B region feature value. The CPU 31 may also employ the distance from the feature value of the A region to the feature value of the B region (see W in FIG. 27 and FIG. 28) as the difference amount.

Alternatively, instead of splitting the theta wave frequency band into two and employing the difference between the feature values obtained from the wave strengths of the resulting bands for the horizontal axis, the CPU 31 may create a coordinate system by splitting the theta wave frequency band into two and employing a fourth ratio, this being a ratio of the feature values obtained from the wave strengths of the resulting bands, for the horizontal axis. The CPU 31 employs an average of the fourth ratio for all measurement timings as found using an arithmetic mean, weighted average, or root-mean-square method, an average of natural logarithms of the fourth ratio for all brain wave measurement timings, or the median value of the fourth ratio as the second reference value.

Pain Testing using Mouse

Figure 30:
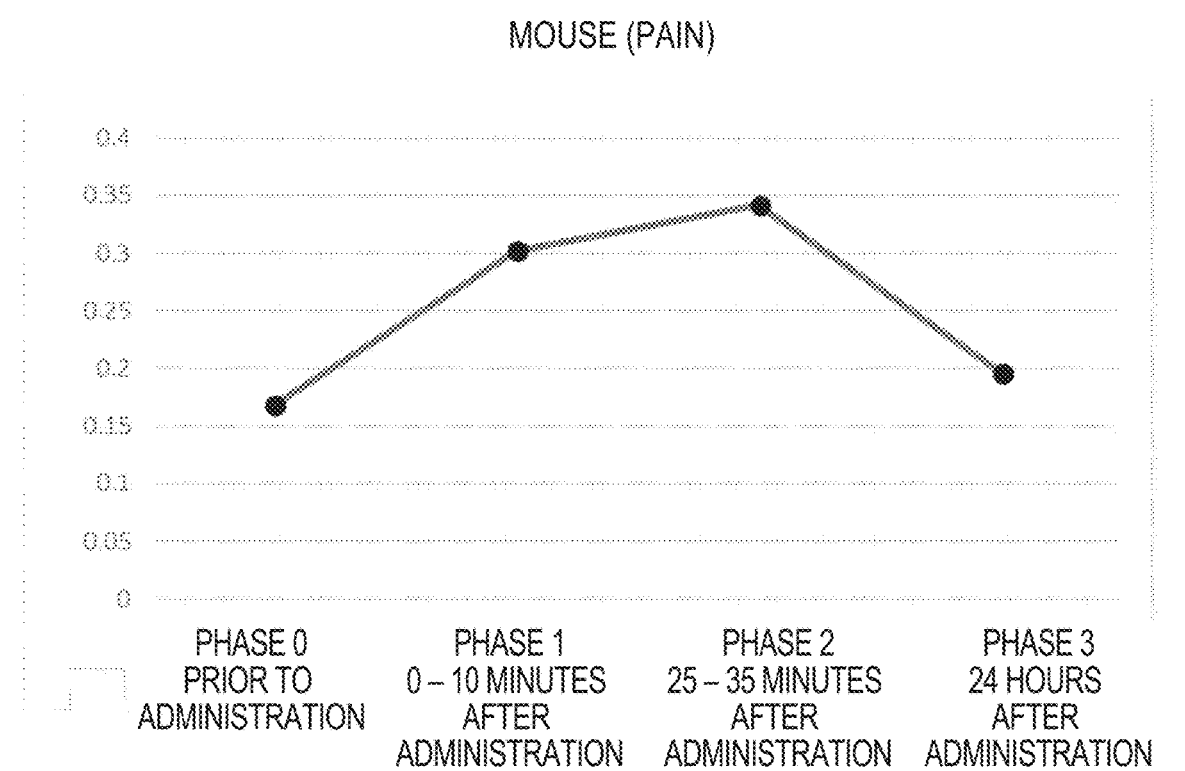
FIG. 30 is a diagram illustrating test results for pain, using a mouse.
Figure 31:
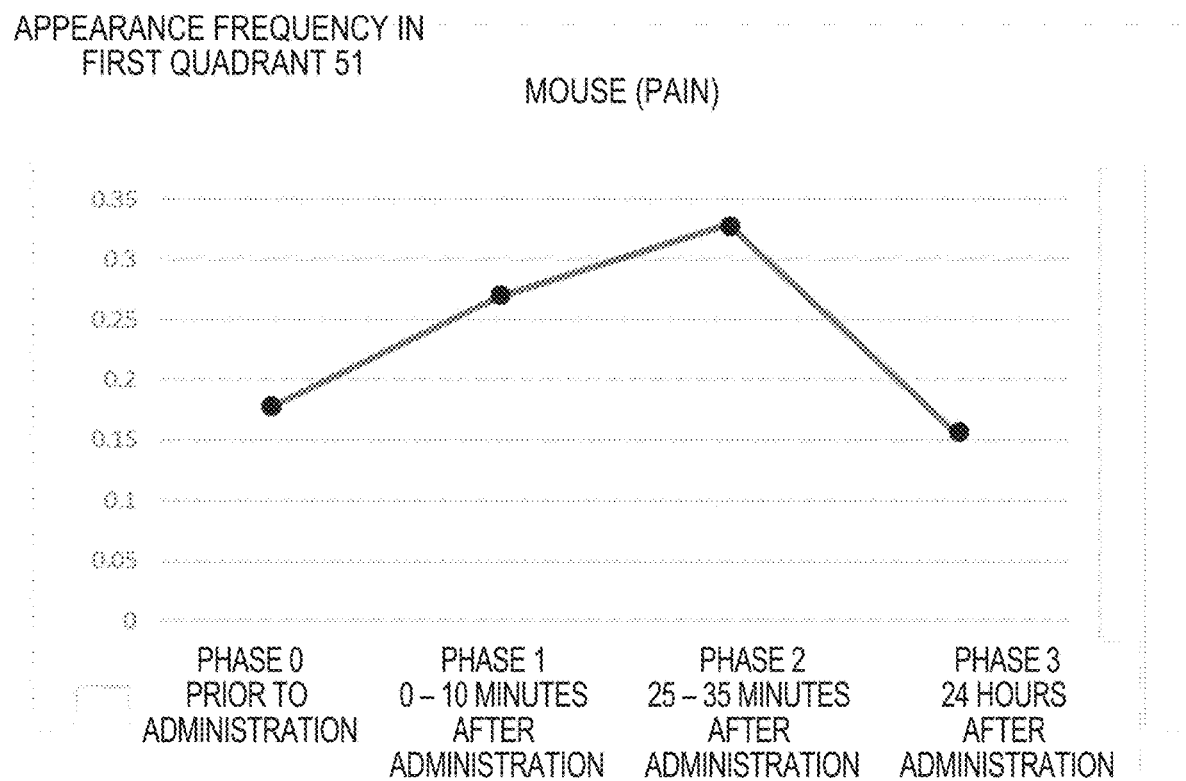
FIG. 31 is a diagram illustrating test results for pain, using a mouse.

FIG. 30 and FIG. 31 are diagrams illustrating test results for pain testing using a mouse. Similarly to the test results illustrated in FIG. 14, FIG. 30 and FIG. 31 are graphs illustrating the appearance frequency with which points appear in the first quadrant 51 in Phase 0 prior to formalin administration and in Phases 1 to 3 after formalin administration. In FIG. 30 and FIG. 31, averages for all brain wave measurement timings are employed as the X axis origin and the Y axis origin, namely as the first reference value and the second reference value. The test results illustrated in FIG. 30 and FIG. 31 are obtained from a different mouse to the mouse used to obtain the test results illustrated in FIG. 14.

Similarly to FIG. 14, FIG. 30 illustrates an appearance frequency of points in the first quadrant 51 in a case in which the second ratio (for example theta/beta) is employed as the X axis. FIG. 31 illustrates an appearance frequency of points in the first quadrant 51 in a case in which a difference amount (for example H in FIG. 27) is employed as the X axis instead of the second ratio. A value obtained by subtracting the minimum power value in a high band from a maximum power value in a low band is adopted as the difference amount for the test results illustrated in FIG. 31. The brain wave analysis device 30 is capable of obtaining similar results to the test results illustrated in FIG. 14 even in cases in which a difference amount is employed for the X axis instead of the second ratio.

Figure 32:
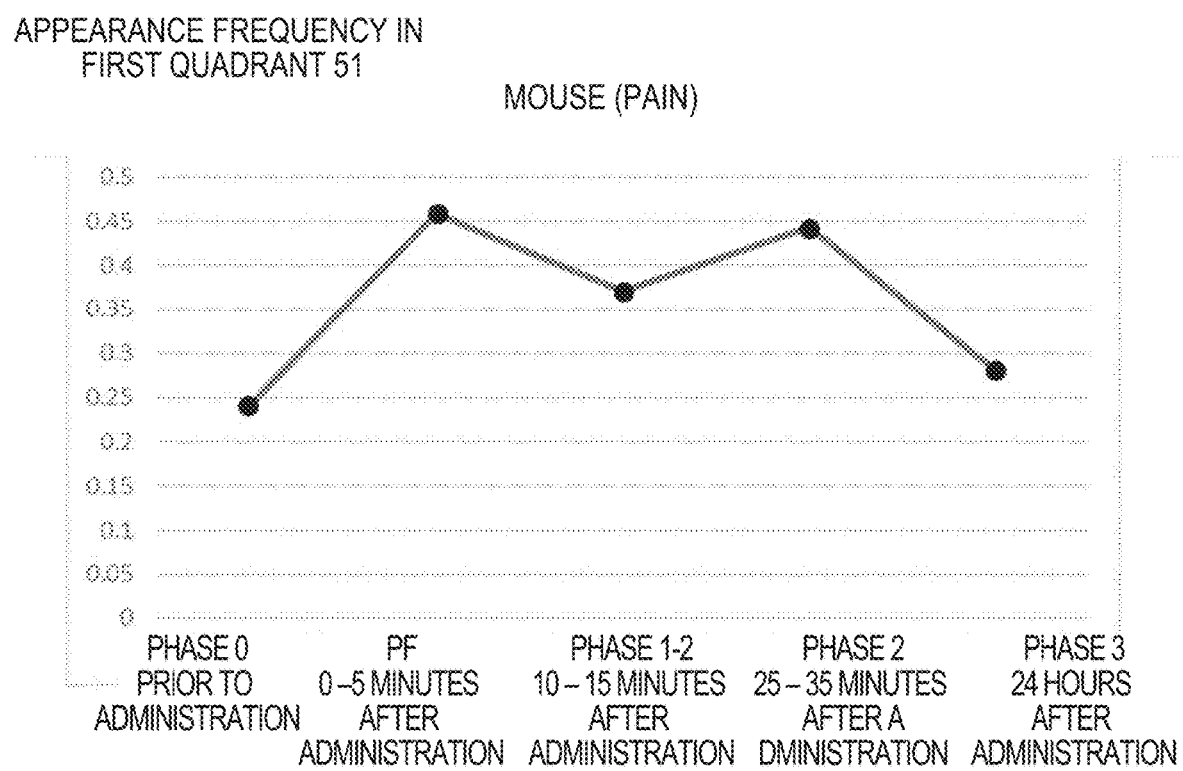
FIG. 32 is a diagram illustrating test results for pain, using a mouse.
Figure 33:
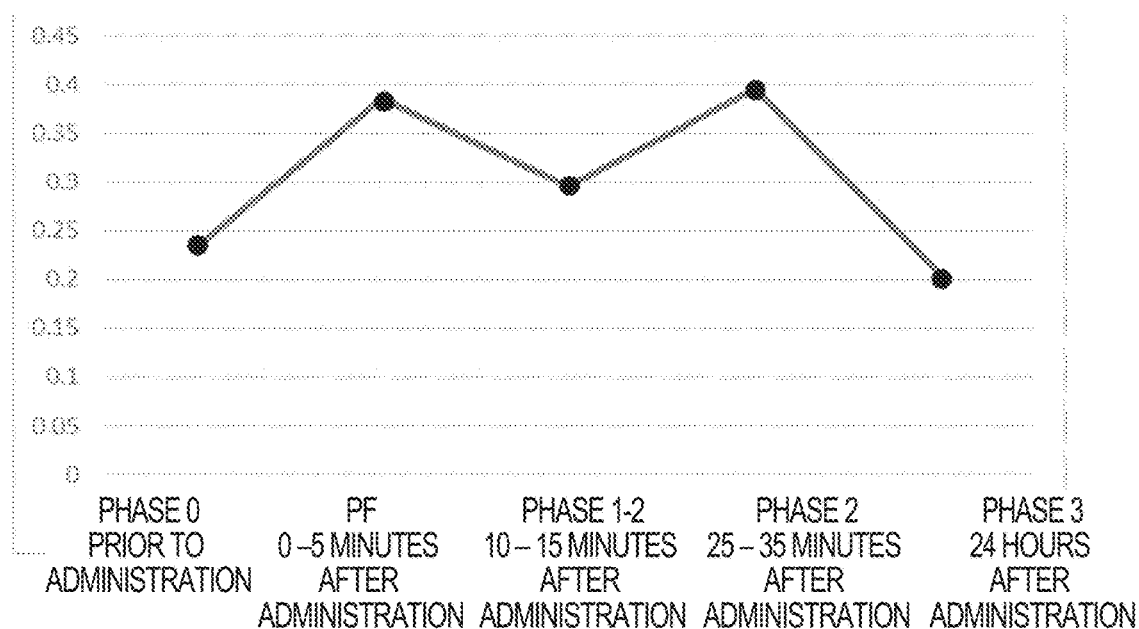
FIG. 33 is a diagram illustrating test results for pain, using a mouse.

FIG. 32 and FIG. 33 are diagrams illustrating test results for pain in the case of a mouse. FIG. 32 and FIG. 33 are graphs illustrating the appearance frequency with which points appear in the first quadrant 51 in a case in which analysis is performed at five time points, namely in the Phase 0 prior to formalin administration, 0 to 5 minutes after administration (PF), 10 to 15 minutes after administration (Phase 1-2: between Phase 1 (0 to 10 minutes after administration) and Phase 2), 25 to 35 minutes after administration (Phase 2), and for 10 minutes 24 hours after administration (Phase 3). The graphs illustrated in FIG. 32 and FIG. 33 employ averages of data prior to formalin administration (at a pre-timing) as the X axis origin and the Y axis origin, namely as the first reference value and the second reference value. Similarly to FIG. 14 and FIG. 30, FIG. 32 illustrates the appearance frequency of points in the first quadrant 51 in a case in which the second ratio is employed for the X axis. Similarly to FIG. 31, FIG. 33 illustrates the appearance frequency of points in the first quadrant 51 in a case in which a difference amount (see H in FIG. 27, for example) is employed instead of the second ratio for the X axis.

As illustrated in FIG. 26, in a case in which a mouse was administered with formalin, theta wave peaks appeared when in pain in Phase 1 and Phase 2. When the mouse brain waves were subjected to frequency analysis and plotted as points on a coordinate system, it could be seen that two peaks appeared when in pain both when the second ratio was employed for the X axis and when a difference amount was employed for the X axis. The brain wave analysis device 30 is thus capable of inferring the mouse state even in cases in which a difference amount is employed for the X axis.

Possible Applications

Next, explanation follows regarding possible applications of the brain wave analysis processing described above.

Focus and Distraction

The brain wave analysis processing is capable of inferring a level of focus in order to ascertain what sort of behavior should be performed in order to improve the level of focus, either for individuals or for groups. For example, the following uses are envisaged in terms of human uses, industrial uses, and animal uses.

Envisaged human uses include application in the monitoring and treatment of disorders such as developmental disorders (ADHD, autism, and the like), sleep disorders, dementia, delirium, depression, and the like. Application is also envisaged relating to the monitoring of mental states such as depressed states, and states relating to sleep or tiredness. Application is envisaged relating to the evaluation of the efficacy of drugs and in the development of drugs using such evaluation. Application is also envisaged relating to state inference for purposes related to health management, self-medication, mindfulness, beauty, and VR sickness. Application is also envisaged relating to nursing care (comfort improvements in care facilities, and efficacy measurement and optimization of rehabilitation). Application is also envisaged relating to practicing technical skills, acquiring technical skills, studying, education, and competitive events.

Furthermore, envisaged industrial uses include application in operational safety, product development, and sensory perception sensors (the detection of abnormal responses to smell, taste, hearing, sight, or touch stimulation).

Envisaged animal uses include application relating to pet health management and human-to-pet communication. Application is also envisaged relating to health management and productivity improvement of livestock.

Pain

It has become possible to evaluate pain using objective indices, thereby enabling the experience of pain and possible pain reduction measures to be ascertained for an individual. For example, the following applications are envisaged.

Application is envisaged relating to the detection of warning sign of disorders with pain such as migraines. Application is also envisaged relating to the quantification of pain, efficiency improvements in treatment by segmentation of pain sensation, and the improved development of novel treatments. Application is also envisaged relating to the evaluation of the efficacy of drugs and in the development of drugs using such an evaluation.

As described above, the brain wave analysis processing of the present exemplary embodiment has the potential for application for various purposes.

The processing described above may also be implemented using dedicated hardware circuitry. In such cases, execution may be performed by a single piece of hardware, or by plural pieces of hardware.

A program to operate the brain wave analysis device 30 may be provided on a computer-readable recording medium such as universal serial bus (USB) memory, a flexible disc, or compact disc read only memory (CD-ROM), or may be provided online over a network such as the internet. In such cases, a program recorded on a computer-readable recording medium is normally forwarded to memory or storage to be stored. Alternatively, the program may be provided as stand-alone application software, or may be incorporated into software for respective devices, each performing one function of the brain wave analysis device 30.

EXPLANATION OF THE REFERENCE NUMERALS

30 brain wave analysis device
31 CPU
32 ROM
33 RAM
34 storage
35 input section
36 display section
37 communication interface
39 bus
40 communication network
50 origin
51 first quadrant
52 second quadrant
53 third quadrant
54 fourth quadrant
60 point
301 computation section
302 inference section

The invention claimed is:

1. A brain wave analysis device comprising:
   no more than one sensing electrode; and
   no more than one reference electrode,
   a computation section configured to compute a first ratio and a second ratio from a spectrum obtained by performing frequency analysis on time-series data of brain waves measured at a predetermined location of a head of a subject using the sensing electrode,
   the first ratio being either:
   a ratio, of a feature value that is a strength of a first wave in a first sub-band of a first frequency band with respect to a feature value that is a strength of a second wave in a second sub-band of the first frequency band wherein the first wave is generated in a stress-induced state of the subject, and wherein the second sub band is higher than the first sub-band, or
   a ratio of a feature value that is a strength of a third wave in the first frequency band with respect to a feature value that is a strength of a fourth wave in a second frequency band, wherein the fourth wave is generated in an awake state of the subject, and
   the second ratio being a ratio of a feature value that is a strength of a fifth wave in a third frequency band, wherein the fifth wave is generated in a sleeping state of the subject with respect to a feature value that is a strength of a sixth wave in the second frequency band, wherein the sixth wave is generated in an awake state of the subject;
   an inference section configured to infer a state of the subject based on the first ratio, a first reference value set using the first ratio, the second ratio, and a second reference value set using the second ratio:
   wherein the state of the subject is either an attentive state in which the first ratio is larger than the first reference value and the second ratio is smaller than the second reference value, a focused state in which both the first ratio and the second ratio are respectively smaller than the first reference value and the second reference value, or a distracted state in which the second ratio is larger than the second reference value;
   the first frequency band includes gamma waves;
   the second frequency band includes beta waves; and
   the third frequency band theta and delta waves.

2. The brain wave analysis device of claim 1, wherein:
   the first reference value is either an average of the first ratio for all measurement timings, an average of the first ratio for a period prior to stimulation, an average of the first ratio for a period of stimulation, an average of the first ratio for a period after the period of stimulation has ended, or an average of the first ratio for a period of non-stimulation; and
   the second reference value is either an average of the second ratio for all measurement timings, an average of the second ratio for a period prior to stimulation, an average of the second ratio for a period of stimulation, an average of the second ratio for a period after the period of stimulation has ended, or an average of the second ratio for a period of non-stimulation.

3. The brain wave analysis device of claim 1, wherein the inference section is configured to infer a level of the state of the subject by further plotting the first ratio on a Y-axis and the second ratio on an X-axis with an origin at the first reference value and the second reference value, and employing at least one of a distance of the point from the origin, a distance of the point from the origin in a direction of the one axis, a distance of the point from the origin in a direction of the other axis, or an appearance frequency with which points appear in the same quadrant within a predetermined period.

4. The brain wave analysis device of claim 1, wherein the gamma waves in the first frequency band range from 31 Hz to 82.25 Hz, the beta waves in the second frequency band range from 13 Hz to 29.75 Hz, the theta waves in the third frequency band range from 3.5 Hz to 6.75 Hz, and the delta waves in the third frequency band range from 0.5 Hz to 2.75 Hz.

5. The brain wave analysis device of claim 1, wherein the spectrum is a spectrum from which a noise component having a third ratio exceeding a third reference value has been removed, the third ratio being a ratio of a feature value that is a strength of a seventh wave in the first frequency band or an eighth wave in the second frequency band with respect to a feature value that is a strength of a ninth wave in a fourth frequency band that is lower than the second frequency band and higher than the third frequency band, wherein the fourth frequency band includes alpha waves.

6. The brain wave analysis device of claim 5, wherein the noise component is a component in which the third ratio exceeds the third reference value, the third ratio being a ratio of a feature value that is a strength of a low gamma wave in the first frequency band or a strength of a high beta wave in the second frequency band with respect to a feature value that is a strength of a low alpha wave in the fourth frequency band.

7. The brain wave analysis device of claim 1, wherein the feature value wave strength is either an average strength of waves belonging to the same frequency band, a maximum strength of waves belonging to the same frequency band, an integrated value of strengths of waves belonging to the same frequency band, or a median value of strengths of waves belonging to the same frequency band.

8. The brain wave analysis device of claim 1, wherein the state of the subject is a state of feeling pain in a case in which both the first ratio and the second ratio are respectively larger than the first reference value and the second reference value.

9. A brain wave analysis device, comprising:
   no more than one sensing electrode; and
   no more than one reference electrode,
   a computation section configured to compute a first ratio and a difference amount or a fourth ratio from a spectrum obtained by performing frequency analysis on time-series data of brain waves measured at a predetermined location of a head of a subject using the sensing electrode,
   the first ratio being either:
   a ratio, of a feature value that is a strength of a first wave in a first sub-band of a first frequency band with respect to a feature value that is a strength of a second wave in a second sub-band of the first frequency band wherein the first wave is generated in a stress-induced state of the subject, and wherein the second sub band is higher than the first sub-band, or
   a ratio of a feature value that is a strength of a third wave in the first frequency band with respect to a feature value that is a strength of a fourth wave in a second frequency band, wherein the fourth wave is generated in an awake state of the subject,
   the difference amount being obtained from feature values that are strengths of tenth and eleventh waves in bands resulting from splitting in two a band of frequency equal to or greater than a third frequency band generated in a sleeping state of the subject and lower than the second frequency band, and the fourth ratio being a ratio of feature values that are strengths of the tenth and eleventh waves in the resulting split bands;

an inference section configured to infer a state of the subject based on the first ratio, a first reference value set using the first ratio, the difference amount, or the fourth ratio, and based on a second reference value set using the difference amount or the fourth ratio;

wherein the state of the subject is either an attentive state in which the first ratio is larger than the first reference value and the difference amount or the fourth ratio is smaller than the second reference value, a focused state in which both the first ratio and the difference amount or the fourth ratio are respectively smaller than the first reference value and the second reference value, or a distracted state in which the difference amount or the fourth ratio is larger than the second reference value;

the first frequency band includes gamma waves;

the second frequency band includes beta waves; and the third frequency band theta and delta waves.

10. The brain wave analysis device of claim 9, wherein the difference amount is a difference between a strength or power value integral of a low frequency portion of the split frequency band and a strength or power value integral of a high frequency portion of the split frequency band, and the fourth ratio is a ratio between strength or power value integral of a high frequency portion of the split frequency band and the strength or power value integral of a low frequency portion of the split frequency band.

11. The brain wave analysis device of claim 9, wherein the difference amount is a difference between a maximum power value of a low frequency portion of the split frequency band and a minimum power value of a high frequency portion of the split frequency band.

12. A brain wave analysis system, comprising:
a data acquisition section configured to acquire time-series data of brain waves measured at a predetermined location of a head of a subject; and
the brain wave analysis device of claim 1.

13. A brain wave analysis program executable by a computer to perform processing, the processing comprising:
measuring brain waves as a time-series data at a predetermined location of a head of a subject using no more than one sensing electrode; and no more than one reference electrode,
computing a first ratio and a second ratio from a spectrum obtained by performing frequency analysis on the time-series data of brain waves,
the first ratio being either:
a ratio, of a feature value that is a strength of a first wave in a first sub-band of a first frequency band with respect to a feature value that is a strength of a second wave in a second sub-band of the first frequency band wherein the first wave is generated in a stress-induced state of the subject, and wherein the second sub band is higher than the first sub-band, or
a ratio of a feature value that is a strength of a third wave in the first frequency band with respect to a feature value that is a strength of a fourth wave in a second frequency band, wherein the fourth wave is generated in an awake state of the subject, and
the second ratio being a ratio of feature value that is a strength of a fifth wave in a third frequency band, wherein the fifth wave is generated in a sleeping state with respect to a feature value that is a strength of a sixth wave in the second frequency band, wherein the sixth wave is generated in an awake state of the subject:
inferring a state of the subject based on the first ratio, a first reference value set using the first ratio, the second ratio, and a second reference value set using the second ratio;
wherein the state of the subject is either an attentive state in which the first ratio is larger than the first reference value and the second ratio is smaller than the second reference value, a focused state in which both the first ratio and the second ratio are respectively smaller than the first reference value and the second reference value, or a distracted state in which the second ratio is larger than the second reference value;

the first frequency band includes gamma waves;

the second frequency band includes beta waves;

the third frequency band theta and delta waves.

14. A brain wave analysis program executable by a computer to perform processing, the processing comprising:
measuring brain waves as a time-series data at a predetermined location of a head of a subject using no more than one sensing electrode and no more than one reference electrode,
computing a first ratio and a difference amount from a spectrum obtained by performing frequency analysis on the time-series data of brain waves,
the first ratio being either:
a ratio, of a feature value that is a strength of a first wave in a first sub-band of a first frequency band with respect to a feature value that is a strength of a second wave in a second sub-band of the first frequency band wherein the first wave is generated in a stress-induced state of the subject, and wherein the second sub band is higher than the first sub-band, or
a ratio of a feature value that is a strength of a third wave in the first frequency band with respect to a feature value that is a strength of a fourth wave in a second frequency band, wherein the fourth wave is generated in an awake state of the subject, and
the difference amount being obtained from feature values that are strengths of tenth and eleventh waves in bands resulting from splitting in two a band of frequency equal to or greater than a third frequency band, wherein the fifth wave is generated in a sleeping state and lower than the second frequency band; and
inferring a state of the subject based on the first ratio, a first reference value set using the first ratio, the difference amount, and a second reference value set using the difference amount,
wherein the state of the subject is either an attentive state in which the first ratio is larger than the first reference value and the difference amount is smaller than the second reference value, a focused state in which both the first ratio and the difference amount are respectively smaller than the first reference value and the second reference value, or a distracted state in which the difference amount is larger than the second reference value;

the first frequency band includes gamma waves;

the second frequency band includes beta waves; and the third frequency band theta and delta waves.

* * * * *